US012767350B1

(12) United States Patent
Coulson et al.

(10) Patent No.: US 12,767,350 B1
(45) **Date of Patent: *Oct. 20, 2026**

(54) AVIATION FUEL CONTAMINANT DETECTION AND PREDICTION SYSTEM

(71) Applicant: Coulson Aviation (USA) Inc, Portland, OR (US)

(72) Inventors: Britton Coulson, Port Alberni (CA); Wayne Coulson, Port Alberni (CA)

( * ) Notice: Subject to any disclaimer, the term of this patent is extended or adjusted under 35 U.S.C. 154(b) by 0 days.

This patent is subject to a terminal disclaimer.

(21) Appl. No.: 19/398,591

(22) Filed: Nov. 24, 2025

(51) Int. Cl.
*B64D 45/00* (2006.01)
*B64D 37/00* (2006.01)
*B64F 1/28* (2006.01)
*G01N 33/28* (2006.01)

(52) U.S. Cl.
CPC ........... *B64D 45/00* (2013.01); *B64D 37/005* (2013.01); *G01N 33/2847* (2013.01); *B64F 1/28* (2013.01)

(58) Field of Classification Search
CPC .. B64D 45/00; B64D 37/005; G01N 33/2847; B64F 1/28
See application file for complete search history.

(56) References Cited

U.S. PATENT DOCUMENTS 7,518,719 B2 4/2009 Sprenger et al.
8,381,779 B1 * 2/2013 Wyler ...................... B64F 1/28 141/192
8,498,750 B2 7/2013 Stevens et al.
8,684,028 B2 4/2014 Perez
8,720,499 B2 5/2014 Kastner et al.
8,897,991 B2 * 11/2014 Geng .................... F02D 19/087 123/1 A
9,109,940 B2 8/2015 Bahorich et al.
12,479,589 B1 * 11/2025 Coulson ................ B64D 37/18
2011/0115649 A1 5/2011 Smith et al.
2011/0130882 A1 6/2011 Perez
2011/0162448 A1 7/2011 McGaughey et al.
2012/0234770 A1 9/2012 Goodwin
2013/0079955 A1 3/2013 Masiello et al.
(Continued)

FOREIGN PATENT DOCUMENTS

GB 2625124 A 6/2024

OTHER PUBLICATIONS

ASTM International, Standard Specification for Aviation Turbine Fuels, 2005, 6 pages.
(Continued)

*Primary Examiner* — Daryl C Pope
(74) *Attorney, Agent, or Firm* — Sterne, Kessler, Goldstein & Fox P.L.L.C.

(57) ABSTRACT

An aircraft-based fuel quality monitoring and alerting system is disclosed herein. The aircraft-based fuel quality monitoring and alerting system can include a first sensor configured to output a first signal corresponding to contamination of fuel entering an aircraft fuel tank through a first fuel inlet, a second sensor configured to output a second signal corresponding to an amount of fuel in the aircraft fuel tank, and a processor configured to determine a relative contamination level of the fuel in the aircraft fuel tank based on the first signal and the second signal. The system can further include an alerting system configured to deliver an alert via a pilot interface inside the aircraft if the relative contamination level is outside a first range.

30 Claims, 14 Drawing Sheets

(56) References Cited

U.S. PATENT DOCUMENTS

| | | | | |
|---|---|---|---|---|
| 2014/0039777 | A1 | 2/2014 | Geng et al. | |
| 2015/0123820 | A1 | 5/2015 | Merle et al. | |
| 2015/0301013 | A1* | 10/2015 | Wiebe ................ | G01N 33/2847 73/61.41 |
| 2019/0127080 | A1 | 5/2019 | Selvarajan et al. | |
| 2022/0107303 | A1 | 4/2022 | Goltzman et al. | |
| 2024/0190579 | A1 | 6/2024 | Fallon | |
| 2024/0321113 | A1 | 9/2024 | Feyereisen et al. | |
| 2025/0110060 | A1* | 4/2025 | Kappa Venkata ........................... | G01N 21/9072 |

OTHER PUBLICATIONS

Avfuel, Rampside Training System, Video reference guide, May 7, 2014, 91 pages.
Parker Velcon, Water-in-Fuel Sensor (WIF), 2019, 2 pages.
Parker Velcon, VCA Fuel Condition Monitoring & Control, 2015, 24 pages.
International Search Report and Written Opinion issued under International Application No. PCT/US2025/043546, mailed Oct. 8, 2025, 10 Pages.

* cited by examiner

AVIATION FUEL CONTAMINANT DETECTION AND PREDICTION SYSTEM

FIELD

The present disclosure is directed to fuel quality monitoring and alerting systems. More specifically, the present disclosure is directed to fuel quality monitoring and alerting systems including components installed on aircraft, such as airplanes and helicopters.

BACKGROUND

Poor fuel quality can be associated with the presence of contaminants, such as water and particulates, in a fuel tank. Poor fuel quality can also be characterized by an inappropriate fuel type that is, for example, a different or lower grade than desirable for the engine. Poor fuel quality can cause failures of components or the entire engine in a variety of vehicles and circumstances, including airborne aircraft.

BRIEF SUMMARY

Poor fuel quality can originate from a fuel source, such as a fuel truck. If the fuel source is contaminated, a vehicle receiving fuel from the fuel source may intake contaminated fuel that can cause premature failures. For example, if an aircraft receives fuel contaminated with water, the water may freeze as the aircraft gains altitude. Water is denser than, for example, jet fuel, and can therefore settle between the jet fuel and the engine. If the water freezes, it can prevent the flow of fuel into the engine, which can cause an engine failure. As another example, a fuel source may contain a different or lower grade of fuel than is desirable, or prescribed by the engine manufacturer, for proper functioning of the engine, and can cause premature wear and subcomponent damage. Also, a jet engine can be inadvertently exposed to aviation gas (Avgas) instead of turbine fuel, and a piston-engine aircraft can be inadvertently exposed to turbine fuel. As another example, Diesel Exhaust Fluid (DEF) can inadvertently enter a fuel truck containing Jet A fuel. As another example, superabsorbent polymer (SAP) can pass through filters on a fuel truck and can clog engine fuel controls. The presence of, for example, water in the aircraft fuel tank can also lead to microbial growth and corrosion. Additionally, surfactants and contaminants in water, such as corrosion inhibitors, detergents, and pipeline carry-over can prevent fuel from separating from water that enters the fuel tank, which can reduce the amount of usable fuel in the fuel tank, deteriorate quantity indication system accuracy, and have other negative effects in fuel related components.

As another example, Sustainable Aviation Fuel (SAF) is increasingly being used to reduce the carbon footprint associated with air travel. SAF generally includes a combination of renewable biomass and waste resources, such as corn grain, oil seeds, algae, agricultural residues, forestry residues, wood mill waste, municipal solid waste streams, wet wastes (e.g., manures, wastewater, treatment sludge), and/or dedicated energy crops. Mixing SAF with conventional fuel types (e.g., Jet-A) inside a fuel tank can produce unsafe percentages of SAF components (e.g., renewable biomass and waste resources) that can hinder engine performance.

Manual sampling techniques to observe or measure fuel quality may not provide a timely indication of contamination. For example, it can take about an hour for water to settle to the bottom of an aircraft fuel tank filled with turbine fuel. Sumping fuel from a low point on the aircraft before the water settles may provide a false indication of fuel quality. Thus, it is possible for an aircraft to takeoff before being able to manually detect contamination. Contaminated fuel, including particulates, water, and improper fuel types, can cause an engine to malfunction or fail.

Alerting the flight crew to poor fuel quality can increase situational awareness and improve decision making. A flight crew in-the-loop fuel quality monitoring system can alert flight crews to incoming poor fuel and can inform flight crews of the impact that the incoming fuel could have on aircraft performance. Allowing flight crews to make fueling decisions (e.g., continue fueling, stop fueling) with improved situational awareness can mitigate engine malfunction and/or failure without negatively impacting operational efficiency.

A combination of flight crew in-the-loop fuel quality monitoring and automated shut-off can balance providing flight crews with sufficient authority to exercise appropriate aeronautical decision making while also providing a protective layer (e.g., automated fuel shut off) if the flight crew is not attentive.

The present disclosure is directed to aircraft-based fuel quality monitoring and alerting systems. In some embodiments, the system includes a sensor configured to output a signal associated with contamination of fuel entering an aircraft through an inlet. The system can further include a processor configured to determine a contamination level of the fuel entering the aircraft based on the output signal. The system can also include an alerting system configured to deliver an alert if the contamination level is outside a predetermined range.

In some embodiments, the system can include a second sensor configured to output a signal associated with contamination of the fuel when the fuel enters the aircraft. Additionally, the system can include a processor configured to determine a second contamination level of the fuel entering the aircraft. In some embodiments, the system can be configured to deliver an alert if the first contamination level is outside the predetermined range and the second contamination level is outside the predetermined range. In some embodiments, the first sensor and second sensor can be disposed inside a first fuel tank inside the aircraft. The first sensor can be disposed within a first wing, and the second sensor can be disposed within a second wing. In some embodiments, the first sensor can be configured to output signals associated with a contamination level of fuel entering a first fuel inlet formed in a first wing, and the second sensor can be configured to output signals associated with a contamination level of fuel entering a second fuel inlet formed in a second wing. In some embodiments, the first and second sensor can be disposed inside an aircraft fuel tank. In some embodiments, the first sensor can be disposed in a first aircraft fuel tank in a first wing, and the second sensor can be disposed in a second aircraft fuel tank in a second wing.

In some embodiments, the alerting system of the present disclosure is configured to deliver a visual alert. In some embodiments, the visual alert can be a text alert. In some embodiments, the alerting system can deliver an aural alert. In some embodiments, the alerting system can be configured to deliver a combination of a visual alert and an aural alert.

In some embodiments, the alerting system can be configured to deliver an alert when a contamination level is outside a predetermined range, and the contamination level can be associated with an amount of water entering the aircraft through the fuel inlet. In some embodiments, the predetermined range can include an amount of water entering the aircraft though a fuel inlet. In some embodiments, the predetermined range can be between 0 PPM and 15 PPM of water. In some embodiments, the processor can be configured to determine the amount of water in the fuel entering the aircraft fuel tank.

In some embodiments, the alerting system of the present disclosure can be configured to deliver an alert to a pilot interface, including a display, indicator, and/or audio system. In some embodiments, the alerting system can be configured to deliver the alert through a wireless communication protocol, such as Bluetooth, WiFi, and/or RF. In some embodiments, the alerting system can deliver an alert from the aircraft to a ground station, such as a ground control station configured to operate a remotely piloted aircraft.

In some embodiments, an aircraft includes a first sensor configured to output a signal associated with contamination of fuel entering an aircraft through a first fuel inlet, a processor configured to determine a first contamination level of the fuel based on the signal, and an alerting system configured to deliver an alert if the first contamination level is outside a predetermined range. In some embodiments, the aircraft can have a fuel inlet formed in a wing, and the first sensor can be disposed in fuel tank in the wing.

The present disclosure is also directed a method for monitoring aircraft fuel quality. In some embodiments, the method can include outputting, by a sensor disposed in an aircraft, a signal associated with contamination of fuel entering an aircraft through a fuel inlet; determining, by a processor, a contamination level of the fuel based on the signal; and delivering an alert, by an alerting system, if the contamination level is outside a predetermined range.

In some embodiments, the alerting system of the present disclosure can be configured to deliver an alert if the contamination level is outside the predetermined range for a predetermined time period. In some embodiments, the alerting system can deliver a first alert if the contamination level is outside the predetermined range for a first predetermined time period, and the alerting system can deliver a second alert if the contamination level is outside the predetermined range for a second predetermined time period. In some embodiments, the first alert is different from the second alert. For example, the first alert can be a visual alert, and the second alert can be an aural alert. In some embodiments, the alerting system can be configured to deliver a first alert if the contamination level is outside a first predetermined range, and to deliver a second alert if the contamination level is outside a second predetermined range, wherein the first predetermined range is different than the second predetermined range. For example, the first predetermined range can be associated with a smaller portion of water entering the fuel tank than the second predetermined range.

In some embodiments, the fuel quality and monitoring system of the present disclosure can include a first sensor configured to output a first signal corresponding to contamination of fuel entering an aircraft fuel tank through a first inlet, and a second sensor configured to output a second signal corresponding to an amount of fuel in the aircraft fuel tank. In some embodiments, the system can include a processor configured to determine a relative contamination level of the fuel in the aircraft fuel tank based on the first signal and the second signal. In some embodiments, the alerting system of the present disclosure can be configured to deliver an alert via a pilot interface inside the aircraft if the relative contamination level is outside a first range.

In some embodiments, the relative contamination level corresponds to an amount of fuel that deviates from a fuel profile. In some embodiments, the fuel profile can include a ratio between a first fuel component and a second fuel component, and the ratio can correspond to a fuel type. In some embodiments, the processor can be configured to classify the fuel entering the aircraft fuel tank as one of a plurality of fuel types. In some embodiments, the first range can correspond to the fuel type entering the aircraft fuel tank. In some embodiments, the first range can be between 0 PPM of water and 15 PPM of water.

In some embodiments, the processor can be configured to determine an incoming fuel contamination level based on the first signal, and the alerting system can be configured to deliver a second alert if the incoming fuel contamination level is outside a second range. In some embodiments, the processor can be configured to determine an incoming fuel contamination level based on the first signal, and the alerting system can be configured to deliver a second alert if the incoming fuel contamination level is outside a second range and the relative contamination level is inside the first range.

In some embodiments, the processor can be configured to determine a predicted contamination level of the fuel in the aircraft fuel tank based on at least one of a fuel flow rate, a period, an expected amount of fuel, the amount of fuel in the fuel tank, or a capacity of the fuel tank. In some embodiments, the expected amount of fuel can be based on the amount of fuel in the fuel tank and a flight plan. In some embodiments, the alerting system can be configured to deliver a second alert if the predicted contamination level of the fuel in the fuel tank is outside the first range.

In some embodiments, the fuel quality monitoring and alerting system disclosed herein can include a controller configured to actuate a valve to prevent fuel from entering the aircraft fuel tank if the relative contamination level of the fuel in the fuel tank is outside the first range. In some embodiments, the alerting system can be configured to deliver a second alert if the controller actuates the valve. In some embodiments, the valve can be disposed in the aircraft.

In some embodiments, an aircraft of the present disclosure includes a fuel tank, a first sensor configured to output a first signal corresponding to components of fuel entering the fuel, and a second sensor configured to output a second signal corresponding to an amount of fuel in the fuel tank. In some embodiments, the aircraft can include a processor configured to determine the components of fuel entering the fuel tank. In some embodiments, the aircraft can include an alerting system including a pilot interface. In some embodiments, the alerting system can be configured to deliver an alert based on the components of fuel entering the fuel tank and the amount of fuel in the fuel tank.

In some embodiments, the processor can be configured to determine a predicted proportion of a first fuel type inside the fuel tank based on at least one of a fuel flow rate, a period, an expected amount of fuel, the amount of fuel in the fuel tank, or a capacity of the fuel tank. In some embodiments, the alerting system is configured to deliver the alert if the predicted proportion of the first fuel type inside the fuel tank is below a minimum proportion. In some embodiments, the minimum proportion is between 0.95 and 0.99. In some embodiments, the first fuel type corresponds to a fuel type that is compatible with the aircraft.

In some embodiments, the aircraft can include a controller configured to actuate a valve to prevent fuel from entering the fuel tank if the predicted proportion of the first fuel is below a minimum proportion. In some embodiments, the controller can be configured to actuate a valve to prevent fuel from entering the fuel tank if the predicted proportion is below a minimum proportion and the controller receives input from a pilot input system. In some embodiments, the controller is configured to actuate a valve to prevent fuel from entering the fuel tank if the predicted proportion is below a minimum proportion for a consecutive number of epochs.

In some embodiments, the processor can be configured to classify the fuel entering the fuel tank as one of a plurality of fuel types. In some embodiments, the alerting system can deliver the alert to a display configured to output text corresponding to the fuel type entering the fuel tank. In some embodiments, the alerting system can be configured to deliver a second alert if the fuel type entering the aircraft is different from a first fuel type. In some embodiments, the alerting system can be configured to deliver the second alert with an alert level corresponding to the fuel type entering the aircraft.

In some embodiments, a fuel quality monitoring and alerting method of the present disclosure can include receiving, by a processor, a first signal corresponding to a contamination level of fuel entering an aircraft fuel tank through a fuel inlet and receiving, by the processor, a second signal corresponding to an amount of fuel in the aircraft fuel tank. In some embodiments, the method can include determining, by the processor, a predicted contamination level of the fuel in the aircraft fuel tank after a period. In some embodiments, the method can include delivering, by the processor, an alert signal to an alerting system if the predicted contamination level is outside a range.

In some embodiments, the method can include transmitting, by the processor or the alerting system, the contamination level of fuel entering the aircraft fuel tank and the amount of fuel in the aircraft fuel tank to a flight data recording system. In some embodiments, the method can include receiving, by the processor, a fuel source signal corresponding to a type of fuel source inputting the fuel into the aircraft fuel tank, and the range corresponds to the type of fuel source. In some embodiments, the method can include receiving, by the processor, a signal corresponding to a location of the aircraft and the range corresponds to the location of the aircraft.

In some embodiments, the processor can receive the first signal from a first sensor configured to sense fluid characteristics of the fuel entering the aircraft fuel tank. In some embodiments, the processor can receive the second signal from a second sensor configured to sense the amount of fuel in the aircraft fuel tank.

DETAILED DESCRIPTION

The present disclosure describes monitoring fuel quality during fueling and delivering an alert, for example, to a crew, such as a flight crew onboard the aircraft. In some embodiments, the fuel quality monitoring and alerting systems disclosed herein delivers an alert to a crew on a ground control station, such as a ground control station configured to operate a remotely piloted aircraft. The embodiments disclosed herein provide timely, accurate, alerts during fueling to prevent the continued input of contaminated fuel.

Figure 1:
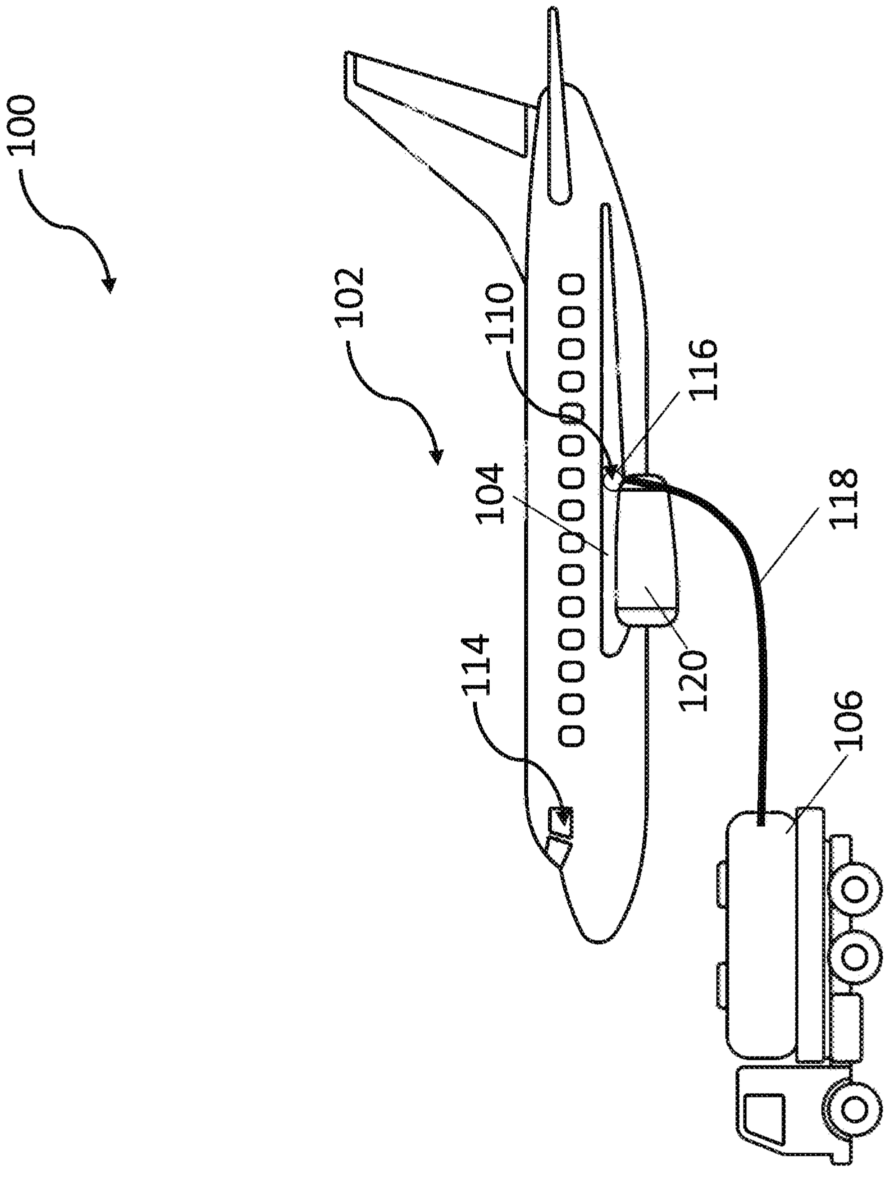
FIG. 1 illustrates a fuel quality monitoring and alerting system for an aircraft according to an embodiment.

FIG. 1 illustrates a fuel quality monitoring system 100 configured to monitor fuel quality as fuel enters an aircraft 102 from a fuel source 106. In some embodiments, fuel quality monitoring system 100 can be an aircraft-based system having one or more components installed on aircraft 100. As a result, fuel quality monitoring system 100 can alert, for example, a flight crew onboard aircraft 102, that fuel entering aircraft 102 is contaminated. For example, fuel can enter an aircraft fuel tank 104 through a fuel inlet 116. The fuel can enter fuel inlet 116 from fuel source 106 through a fuel line 118. Fuel source 106 can be, for example, a fuel truck or a fixed fueling station. In some embodiments, the fuel source can be another aircraft, such as an aircraft configured for aerial refueling.

Fuel stored in fuel source 106 can be contaminated when, for example, fuel source 106 contains water, an improper fuel type, or other particulates. Contaminants can enter an aircraft fuel tank 104 through fuel line 118, which can cause an engine 120 to malfunction if, for example, water freezes during flight and blocks fuel from entering engine 120.

To deliver an alert of contaminated fuel entering aircraft 102, fuel quality monitoring system 100 can include one or more sensors 110 configured to output signals associated with the contamination of fuel entering aircraft 102. In some embodiments, sensor 110 can be disposed in fuel inlet 116. In some embodiments, sensor 110 can be disposed in aircraft fuel tank 104. In some embodiments, sensor 110 can be disposed in fuel line 118. In some embodiments, sensor 110 can be removably disposed in fuel inlet 116. In some embodiments, sensor 110 can be removably coupled to fuel inlet 116 (e.g., at fuel inlet's 116 collar). For example, in some embodiments, sensor 110 can be coupled inline (e.g., inline with fuel line 118) to fuel inlet 116 without being installed inside aircraft 102. In some embodiments, sensor 110 can be disposed in engine 120 fuel lines, cross flow valves, manifolds, transfer pumps, Auxiliary Power Unit feed lines and/or transfer pumps. In some embodiments, sensor 110 can be disposed in fuel source 106 (e.g., fuel truck, fuel cart, hydrant dispenser, etc.)

Sensor 110 can be any sensor configured to output signals associated with contamination levels of a fuel. In some embodiments, for example, sensor 110 can be configured to output signals corresponding to an amount of a contaminant in the fuel, such as water, microbial growth, incorrect fuel type, fuel foaming, etc. In some embodiments, sensor 110 is part of an optical system configured to output signals associated with the light entering the sensor at a predetermined angle. In some embodiments, sensor 110 can be a pressure sensor. In some embodiments, sensor 110 can form part of an electrical system configured to output signals associated with the resistance of a fluid.

Depending on the contamination of the fuel entering aircraft fuel tank 104, fuel quality monitoring system 100 can deliver an alert, for example, via a pilot interface 114. Pilot interface 114 can be, for example, a display configured to output text, an indicator such as a light, and/or a speaker system configured to output an aural alert. Although FIG. 1 illustrates pilot interface 114 inside aircraft 102, pilot interface 114 can be separate from aircraft 102. For example, in some embodiments, aircraft 102 is a remotely piloted aircraft and pilot interface 114 is part of a ground control station configured to operate a remotely piloted aircraft. For example, pilot interface 114 can be part of a ground control station located near a first airport, and aircraft 102 can be located and receiving fuel at a second airport. In some embodiments, pilot interface includes an electronic flight bag, such as a mobile device or tablet, configured to execute a software application. Although FIG. 1 illustrates a fixed-wing aircraft, aircraft 102 can be a helicopter, tiltrotor, or any other aircraft configured to receive fuel.

Figure 2:
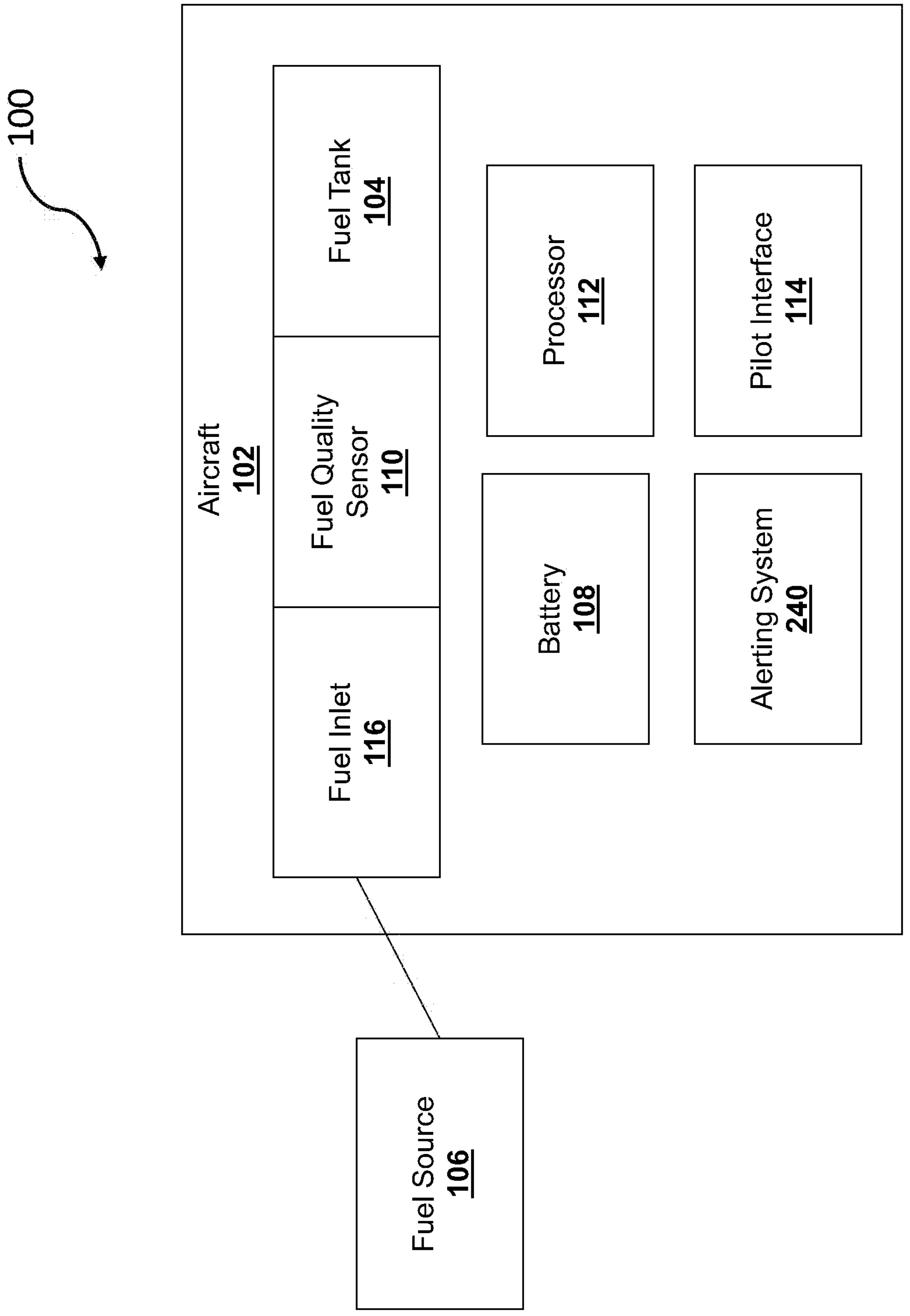
FIG. 2 illustrates a system block diagram of the fuel quality monitoring and alerting system according to an embodiment.
Figure 3:
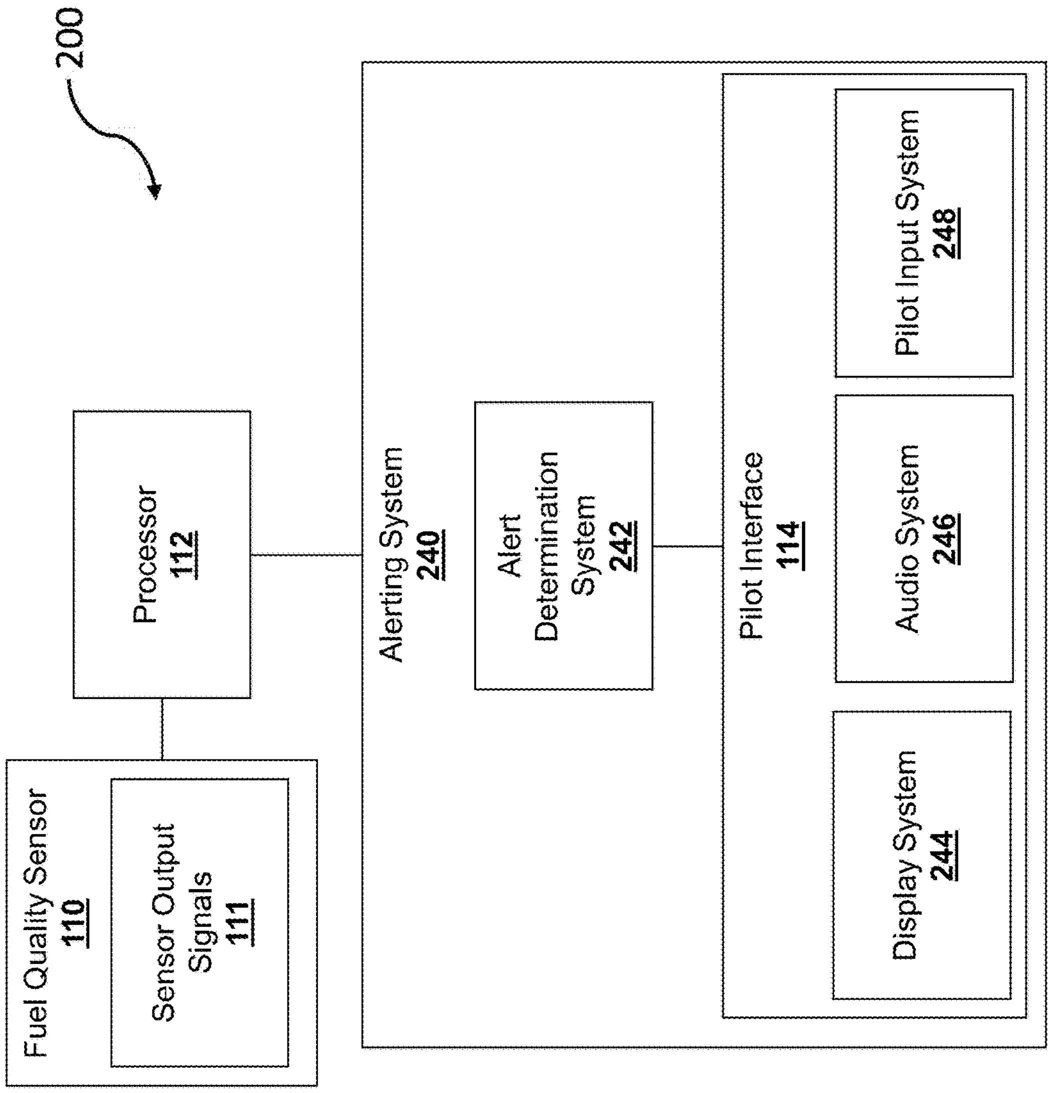
FIG. 3 illustrates a system block diagram of sub-systems of the fuel quality monitoring and alerting system according to an embodiment.

As shown in FIGS. 2-3, for example, fuel quality monitoring system 100 can include a battery 108, a processor 112, and an alerting system 240. Battery 108 can be, for example, auxiliary power unit configured to power electrical systems in aircraft 102. In some embodiments, battery 108 can be configured to power processor 112 and a separate battery can be configured to power other electrical systems, such as the flight display, speakers, autopilot, and passenger entertainment devices. In some embodiments, battery 108 can power processor 112 and alerting system 240. In some embodiments, a first battery can power processor 112 and a second battery can power alerting system 240.

In some embodiments, as shown in FIG. 3, fuel quality sensor 110, processor 112, and alerting system 240 can be characterized as a sub-system 200. Processor 112 can be configured to determine contamination levels of fuel entering aircraft fuel tank 104 based on sensor output signals 111 output by one or more sensors 110. Alerting system 240 can be configured to receive contamination levels from processor 112. In some embodiments, processor 112 executes alerting system 240. In some embodiments, a first processor determines a contamination level of the fuel entering aircraft 102, and a second processor executes alerting system 240.

Alerting system 240 can include an alert determination system 242. Alert determination system 242 can determine if an alerting condition is satisfied based on the contamination levels determined by processor 112. In some embodiments, alert determination system 242 can be configured to determine that an alerting condition is satisfied if the contamination level is outside a predetermined range, for example, above or below a threshold value. Further, alerting system 240 can be configured to deliver an alert if the contamination level is outside a predetermined range. In some embodiments, the predetermined range can be, for example, between 0 and 20 PPM of water. In some embodiments, the predetermined range can be, for example, between 0 and 15 PPM of water. In some embodiments, the predetermined range can be, for example, between 0 and 10 PPM of water. In some embodiments, the predetermined range can be, for example, between 0 and 20 PPM of superabsorbent polymer and/or a predetermined surfactant. In some embodiments, the predetermined range can be, for example, between 0 and 15 PPM of superabsorbent polymer and/or a predetermined surfactant.

In some embodiments, the predetermined range can be an amount of a fuel type. In some embodiments, the predetermined range can be between 0 and 15 PPM of Diesel Exhaust Fuel, JET-A, 100LL, and/or Sustainable Aviation Fuel (SAF).

Alerting system 240 can deliver an alert to pilot interface 114. Pilot interface 114 can include a display system 244, an audio system 246, and/or a pilot input system 248. Display system 244 can be configured to output text, such as an alert reading "FUEL," "POOR FUEL QUALITY," "STOP FUEL," "CHECK FUEL," "CONTAMINATED FUEL," or any other message that can inform a flight or operational crew that the fuel entering aircraft 102 is contaminated or of insufficient quality or grade. In some embodiments, display system 244 can be configured to output text in different colors indicating the severity of the contamination. For example, display system can be configured to output a first visual alert having a first color, and a second visual alert having a second color. Flight crews can understand the first color to indicate an advisory alert, and the second color to indicate a warning alert of higher urgency than the advisory alert. Display system 244 can include a Primary Flight Display, a Secondary Flight Display, a Multi-Function Display, an ADS-B Display a Multi-Function Control and Display Unit, a Heads-Up Display, or any other display in aircraft 102 or a ground control station.

Audio system 246 can be configured to output similar messages as display system 244 through a speaker, headset, and/or other audio output device. In some embodiments, audio system 246 can be configured to beep in addition to, or instead of, outputting a message. Audio system 246 can be a standalone alert output source, or can complement display system 244. For example, if a flight crew does not see a visual alert on display system 244 (e.g., within a set period of time), delivering an aural alert through audio system 246 can help increase the likelihood that the flight crew will act on the alert and stop fueling.

Pilot input system 248 can be configured to receive input from a crew to, for example, extinguish an alert, record data associated with an alert, and/or reset alerting system 240.

In some embodiments, pilot interface 114 includes an electronic flight bag including display system 244, audio system 246, pilot input system 248, or any combination therein. For example, alerting system 240 can be configured to deliver an alert to an electronic flight bag through a wireless communication protocol, such as Bluetooth or Wi-Fi. As another example, alerting system 240 can be stored on an electronic flight bag and accessible as a software application, and processor 112 can be configured to deliver contamination levels to the electronic flight bag. Not all aircraft are equipped with a pilot interface capable of receiving contamination levels from processor 112, and retrofitting such aircraft can be costly. Integrating sub-system 200 with pilot interface 114 including an electronic flight bag can allow aircraft owners and operators to equip a wide variety of aircraft with the fuel quality monitoring and alerting systems and methods disclosed herein.

Figure 4:
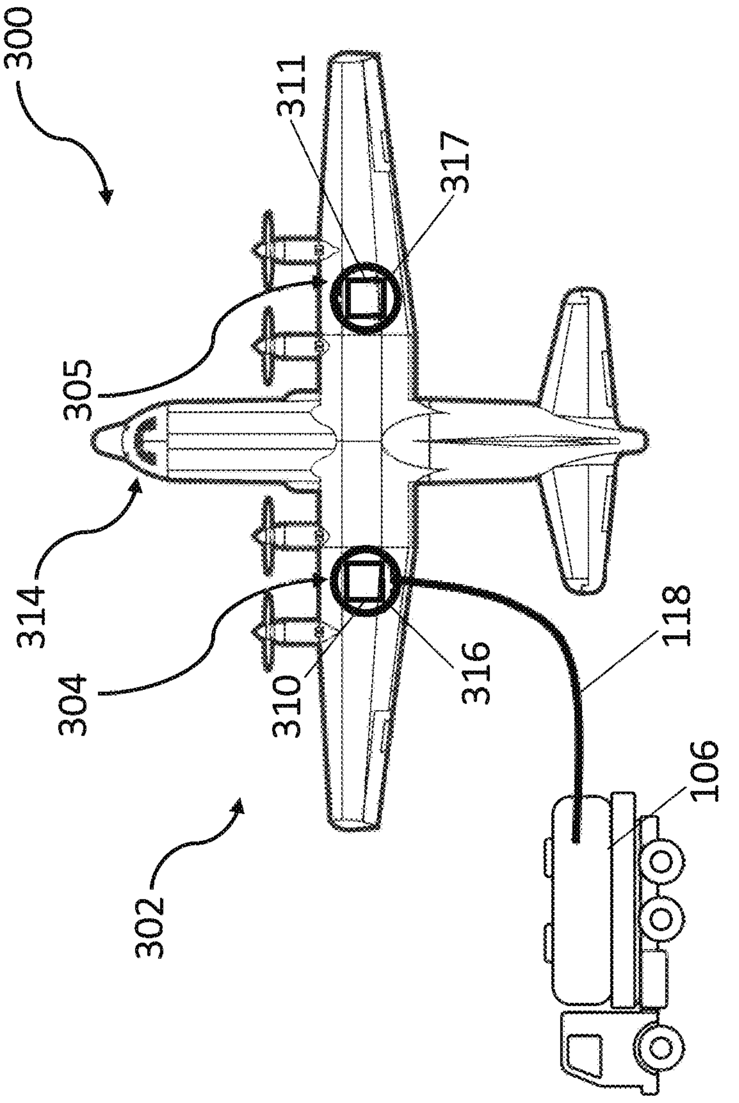
FIG. 4 illustrates a fuel quality monitoring and alerting system for an aircraft according to an embodiment.

In some embodiments, systems disclosed herein can be integrated on aircraft utilizing single point fueling, as illustrated in FIG. 1. Single point fueling typically involves delivering fuel through a single fuel inlet, for example, formed in a lower surface of a wing or the fuselage, and a valving system to direct it into the aircraft's fuel tank(s). However, not all aircraft are equipped with, or readily retrofit to include, a single point fueling system. The systems and methods disclosed herein can also be applied to aircraft configured for over-wing fueling, such as illustrated in FIG. 4. Over-wing fueling typically involves a fuel inlet formed on the top surface of each wing. Because each wing has a fuel inlet on its top surface, the fuel can flow into the aircraft's tanks under gravity.

As shown in FIG. 4, a fuel quality monitoring and alerting system 300 can include an aircraft 302 having a first fuel inlet 316 and a second fuel inlet 317. Both first fuel inlet 316 and second fuel inlet 317 can be formed in an upper surface of wings of aircraft 302. First fuel inlet 316 and second fuel inlet 317 can be configured to receive fuel, for example, from fuel source 106 via fuel line 118, which can engage first fuel inlet 316 and second fuel inlet 317 by extending over the wings on aircraft 302. For example, a fuel truck operator can place a ladder proximate to a first wing including first fuel inlet 316. Using the ladder, the fuel truck operator can raise the fuel line up to first fuel inlet 316 and dispense fuel into a first aircraft fuel tank 304. After dispensing fuel into first aircraft fuel tank 304, the fuel truck operator can reposition the ladder and raise fuel line 118 up to second fuel inlet 317 to dispense fuel into second aircraft fuel tank 305.

Aircraft 302 can include a first sensor 310 disposed in first fuel inlet 316 configured to output signals associated with contamination of fuel entering first aircraft fuel tank 304. Aircraft 302 can further include a second sensor 311 disposed in second fuel inlet 317 configured to output signals associated with contamination of fuel entering second aircraft fuel tank 305. Although the fuel entering first aircraft fuel tank 304 and second aircraft fuel tank 305 can come from the same fuel source 106, the contamination levels can be different. For example, if fuel source 106 contains water, the water can sink below the fuel because water is generally denser than fuels used to power jet and piston aircraft. If fuel line 118 draws fuel from a bottom of fuel source 106, first aircraft fuel tank 304 might intake water, and second aircraft fuel tank 305 might not because the water in fuel source 106 went into first aircraft fuel tank 304.

Accordingly, alerting system 240 can be configured to deliver an alert if the contamination level of the fuel entering first aircraft fuel tank 304 is outside a predetermined range and to deliver an alert if the contamination level of the fuel entering second aircraft fuel tank 305 is outside a predetermined range. Alerting system 240 can further be configured to output alerts associated with first aircraft fuel tank 304 and second aircraft fuel tank 305. For example, alerting system can be configured to output an aural alert announcing "RIGHT TANK FUEL," "CHECK RIGHT TANK FUEL," "STOP FUEL RIGHT TANK," CONTAMINATED FUEL RIGHT TANK," or any other message alerting the crew of contaminated fuel entering aircraft 302, and where the contaminated fuel is being dispensed.

Although the crew may be able to see which wing is receiving fuel when they receive an alert in some circumstances, some conditions can cause the flight crew's perception of the fueling to conflict with where alerting system 240 identified contaminated fuel. For example, as discussed in more detail below, alerting system 240 can be configured to deliver an alert if the contamination level is outside a predetermined range for a predetermined period. A fuel truck operator could switch to fueling a different tank during the predetermined period, and a location specific alert could direct the flight or ground crew to the first tank that received contaminated fuel. As another example, the flight or ground crew may be reviewing a pre-flight checklist and not actively looking at display system 244. By the time the crew sees the alert, the fuel truck operator could have switched to fueling a different tank, or could have completed fueling. Identifying the location of the contaminated fuel in aircraft having a multi-source fueling system can prevent flight crews from checking the wrong tank and concluding that the fuel quality is acceptable. Location specific alerts can also prevent crews from emptying both tanks, when only one tank contained contaminants, which can save time and reduce costs.

Figure 5:
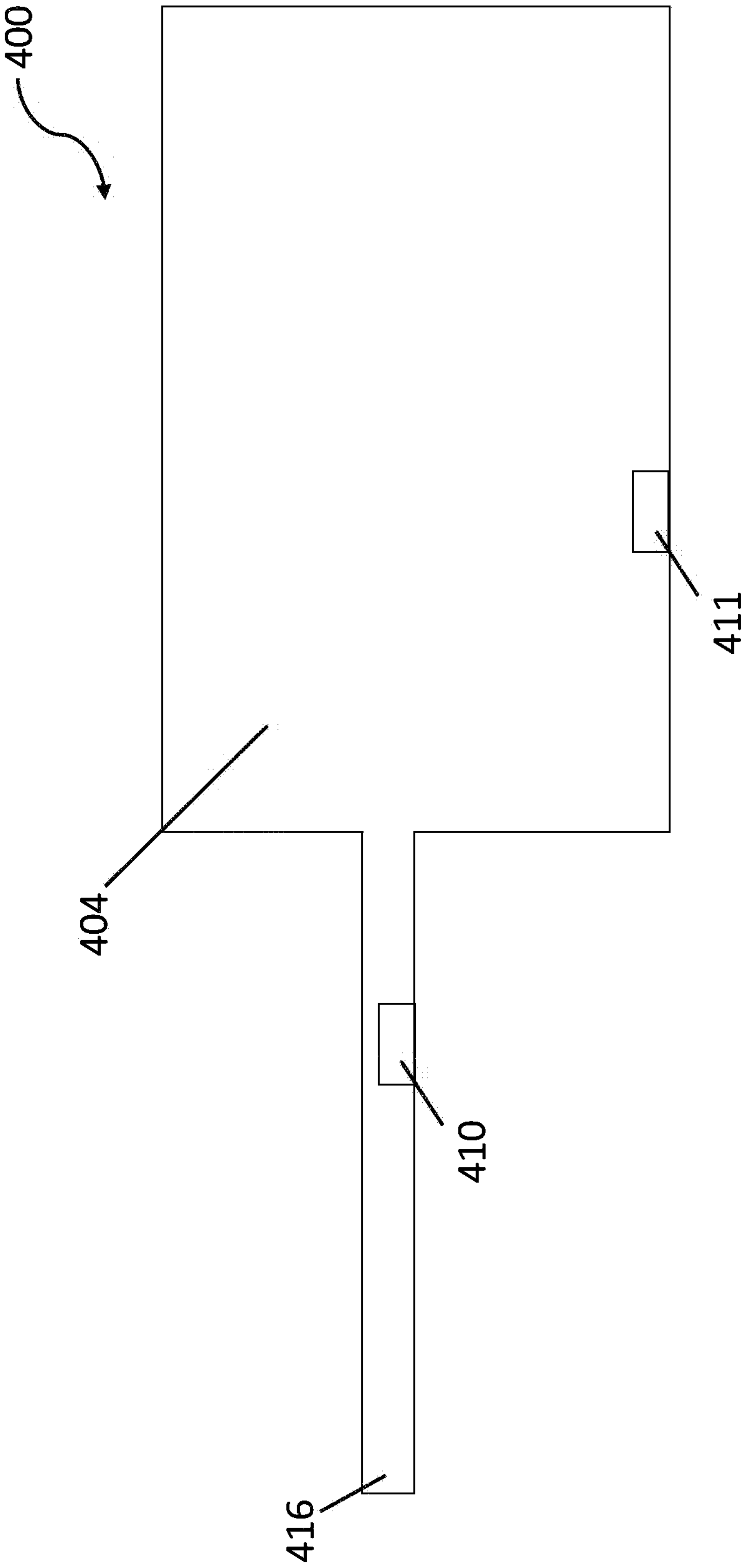
FIG. 5 illustrates a fuel tank with a fuel inlet according to an embodiment.

As shown for example in FIG. 5, in some embodiments, aircraft 102 can include a fuel system 400 having a first sensor 410 disposed in a fuel inlet 416 and/or a second sensor 411 disposed in aircraft fuel tank 404. First sensor 410 can be configured to output signals associated with the contamination of fuel entering fuel inlet 416, and second sensor 411 can be configured to output signals associated with the contamination level of fuel entering aircraft fuel tank 404. Although the fuel entering fuel inlet 416 is the same fuel entering aircraft fuel tank 404 shortly after passing fuel inlet 416, first sensor 410 and second sensor 411 can complement each other, or provide redundancy, to improve the accuracy of alerting system 240. For example, fuel passing through fuel inlet 416 can be more turbulent than the same fuel rising within aircraft fuel tank 404. Increased turbulence can result in unstable output signals from first sensor 410 caused by the rapid and volatile movement of fuel. Second sensor 411, while potentially exposed to a more stable fuel sample, can, however, introduce delays due to the time required for fuel to rise within the tank to second sensor 411. Together, first sensor 410 and second sensor 411 can complement each other to mitigate false alerts while also providing timely alerts of contaminated fuel.

In some embodiments, first sensor 410 and/or second sensor 411 can be disposed at the bottom of fuel tank 104 (sensor 411 is shown for example in FIG. 5). Sensor 410/411 disposed at the bottom of fuel tank 104 can be exposed to contaminants, such as water, that are denser than fuel (e.g., Jet-A, 100 LL). Because some contaminants sink to the bottom of fuel tank 104, sensor 410/411 disposed at the bottom of fuel tank 104 can be exposed to a higher proportion of contaminants relative to sensor 410/411 disposed at fuel inlet 416. In some embodiments, alerting system 240 can be configured to deliver an alert based on signals output by sensor 410/411 disposed at the bottom of fuel tank 104. In some embodiments, for example, alerting system 240 can be configured to deliver an alert instructing the flight crew to sump the fuel tank 104 to remove contaminants from fuel tank 104 to remove contaminants from fuel tank 104.

In some embodiments, first sensor 410 and second sensor 411 can both be disposed in fuel inlet 416 to similarly improve accuracy and mitigate false alerts. Alerting system 240 can be configured to deliver an alert if a contamination level associated with a first sensor is outside a predetermined range and a contamination level associated with a second sensor is outside a predetermined range. Likewise, in some embodiments, first sensor 410 and second sensor 411 can both be disposed in aircraft fuel tank 404.

Figure 6:
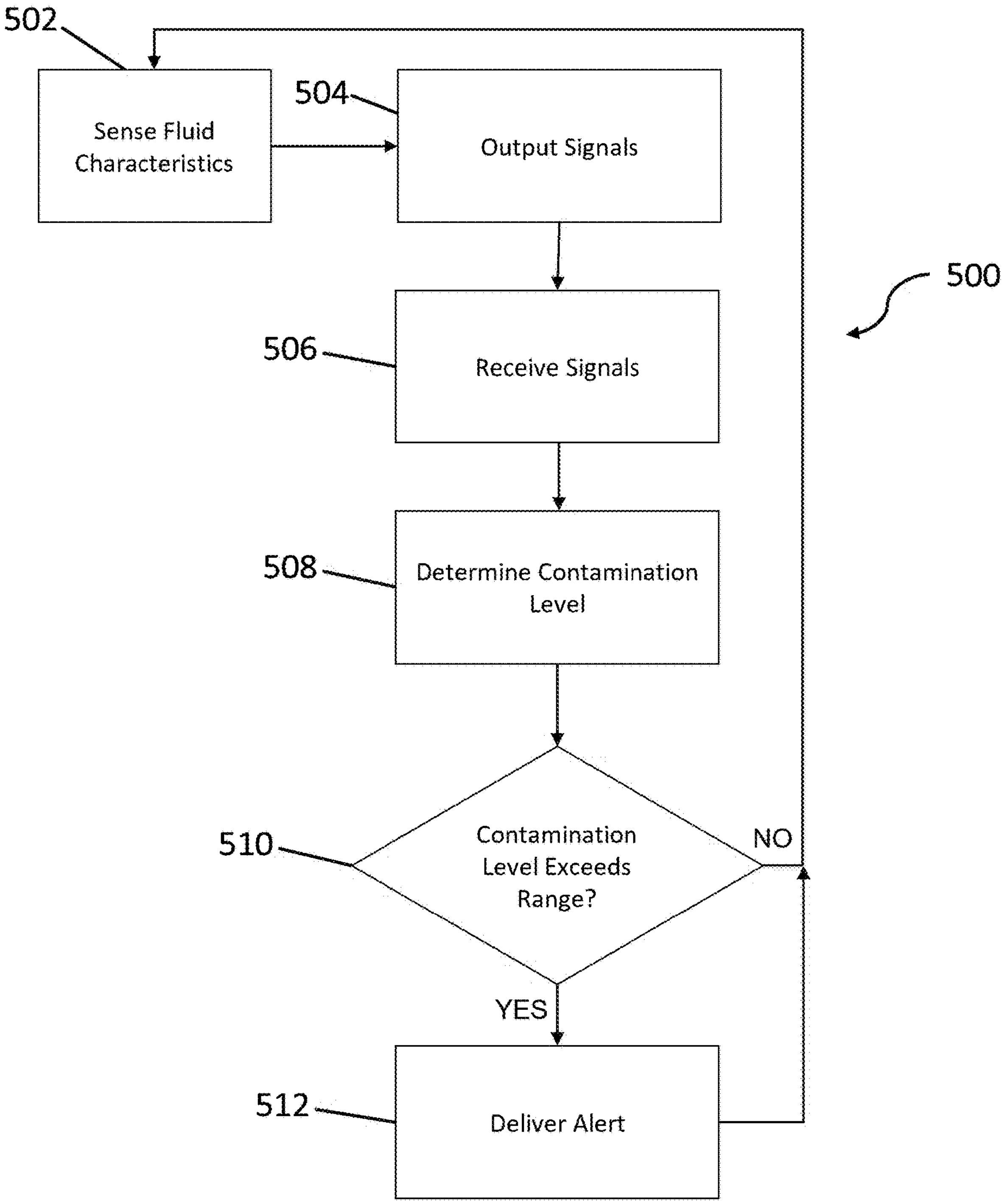
FIG. 6 is a flowchart of a fuel quality monitoring and alerting method according to an embodiment.

In some embodiments, the fuel quality monitoring and alerting system disclosed herein can execute an alerting method 500 resulting in alerting system 240 delivering 512 an alert. As shown in FIG. 6, for example, alerting method 500 can include sensing 502 fluid characteristics. Sensing 502 fluid characteristics can involve measuring the resistance of the fluid, for example, as it passes through fuel inlet 116. In some embodiments, sensing 502 fluid characteristics involves measuring light transmitted through the fluid at a predetermined angle, measuring the pressure of a volume of the fluid, or measuring any other characteristic of a fluid that can indicate the purity, or conversely, the contamination, of that fluid.

For example, measuring the amount of light reflecting through a fluid at a predetermined angle can indicate solid contaminants in the fluid. Further, measuring the amount of light refracting through a fluid can indicate the presence of liquid contaminants. Light can refract through pure fuel at a first angle, but if the fuel tank contains water mixed with the fuel, the light can refract at a second angle different from the first angle, indicating the presence of a liquid contaminants.

After sensing 502 fluid characteristics, alerting method 500 can include outputting 504 signals associated with the fuel characteristics. For example, sensor 110 can output 504 a voltage signal that can be correlated with a resistance of the fluid, the pressure of a volume of the fluid, or the amount of light received by part of sensor 110. Outputting 504 signals can involve outputting one or more signals associated with one or more fluid characteristics that together can be associated with a contamination of the fuel. For example, sensor 110 can output 504 a first signal associated with the amount of light reflected through the fuel at a first angle, and a second signal associated with the amount of light refracted through the fuel at a second angle.

Alerting method 500 can include receiving 506 signals, which can be associated with the contamination of the fuel in aircraft fuel tank 104. In some embodiments, the signals can come from a single sensor. In some embodiments, the signals can come from a first sensor and a second sensor. In some embodiments, processor 112 receives 506 signals and determines 508 a contamination level based on the received signals. Processor 112 can receive 506 multiple output signals 111 per epoch, and can determine 508 multiple contamination levels based on output signals 111, or can determine 508 a single contamination level based on multiple output signals 111. In some embodiments, aircraft 102 includes a first processor configured to receive 506 signals from sensor 110, and a second processor to determine 508 a contamination level based on the received signals. In some embodiments, aircraft 102 includes a first processor configured to receive 506 signals from sensor 110, and a ground control station includes a second processor configured to determine 508 contamination levels based on the received signals. In some embodiments, processor 112 can be integrated on a ground control station, and configured to receive 506 signals from sensor 110, and determine 508 a contamination level of the fuel. As discussed throughout this disclosure, sensor 110 can include one or more sensors of the same or different types.

Alerting method 500 can include evaluating 510 whether the contamination level exceeds a predetermined range. In some embodiments, processor 112 evaluates 510 whether the contamination level exceeds a predetermined range. The predetermined range can be a range of electrical resistance values, a range of pressure values, a range of lumens, and/or a range of values associated with a characteristic of a fluid that can be correlated with the contamination of the fluid. If the contamination level is within the predetermined range, alerting method 500 can restart with sensing 502 fluid characteristics.

If the contamination levels are outside a predetermined range, alerting method 500 can include delivering 512 an alert. In some embodiments, alerting method 500 can include delivering 512 an alert if the contamination levels associated with a first sensor are outside a predetermined range and the contamination levels associated with a second sensor are outside a predetermined range. In some embodiments, alerting system 240 delivers 512 an alert. Alerting system 240 can be executed on processor 112 configured to receive 506 output signals 111, or can be executed on a separate processor. In some embodiments, aircraft 102 can include processor 112, and a ground control station can include alerting system 240. Delivering 512 an alert can involve displaying a text message on display system 244, issuing an aural alert through audio system 246, illuminating a light in pilot interface 114, or any combination therein.

In some embodiments, sensor 110, processor 112, and alerting system 240 can operate at different frequencies. For example, sensor 110 can output 504 signals at 100 Hz, and processor 112 can determine 508 contamination levels and evaluate 510 whether the contamination levels are outside a predetermined range at 1 Hz. By outputting 504 signals at a high rate, sensor 110 can accurately capture the characteristics of the potentially contaminated fuel as it flows into aircraft fuel tank 104. If the rate were too low, sensor 110 might not capture variability in the fuel introduced by water or particulates. Signals output 504 by sensor 110, however, can include noise introduced by, for example, the non-uniform flow of fuel through fuel inlet 116. Processor 112 can determine 508 a contamination level of the fuel by filtering signals it receives 506 from sensor 110, to reduce noise and variability not attributed to contamination. As a result, processor 112 can accurately determine 508 a contamination level and evaluate 510 whether the contamination level is outside a predetermined range. Balancing the rates of sensor 110 and processor 112, or other processors discussed herein, can mitigate potential false alerts that could unnecessarily delay fueling and add time and costs to operating aircraft 102. Although alerting method 500 is described with respect to aircraft 102, alerting method 500 can apply to aircraft 302, and/or any aircraft configured to receive fuel.

Figure 7:
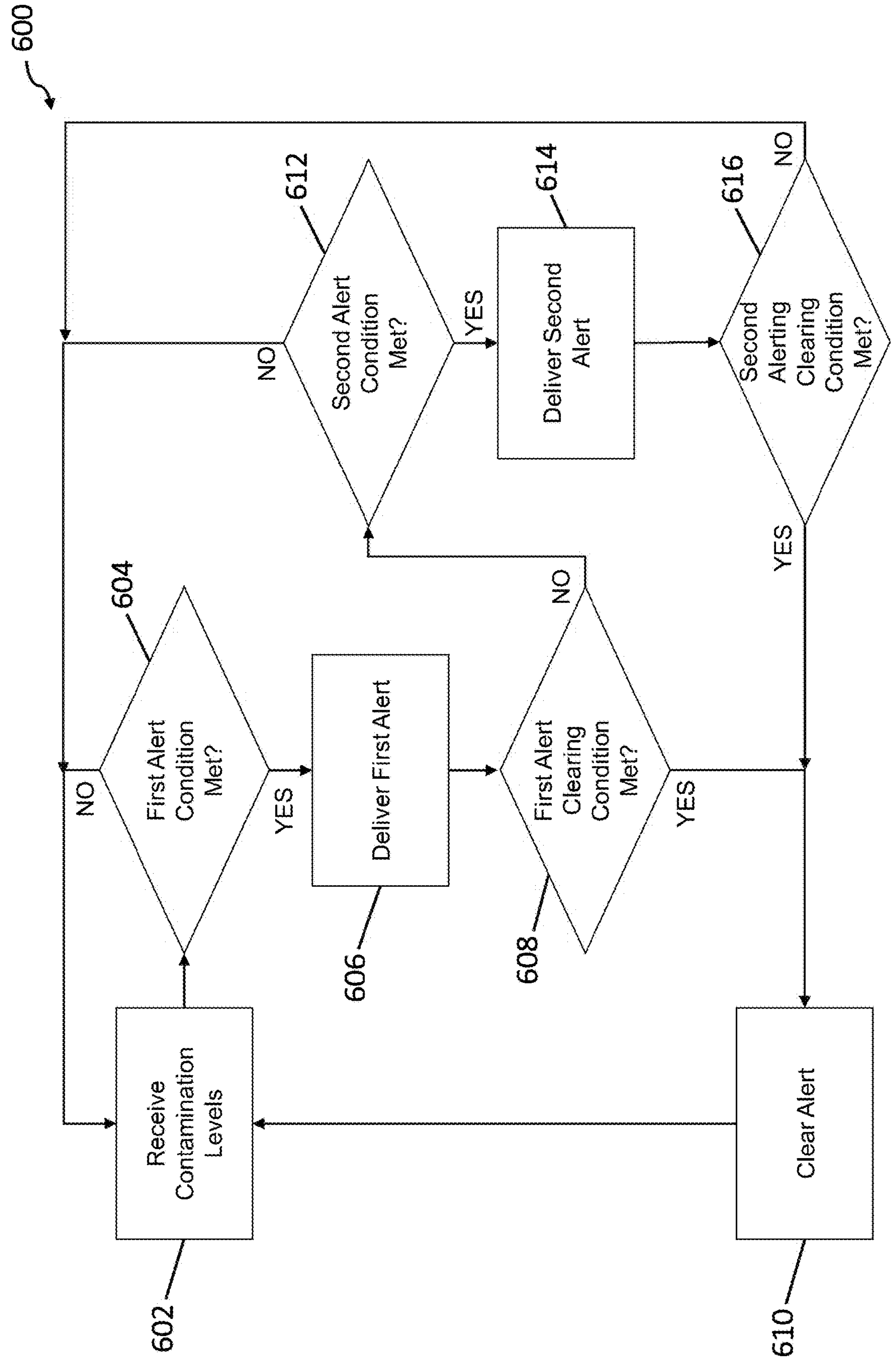
FIG. 7 is a flowchart of an alert sequencing and clearing method for a fuel quality monitoring and alerting system according to an embodiment.

To further provide accurate alerts of contaminated fuel and quickly bring the alert to the attention of the flight crew, the embodiments disclosed herein can include an alert sequencing and clearing method 600. Referring to FIG. 7, alert sequencing and clearing method 600 can include receiving 602 one or more contamination levels. As discussed, processor 112 can receive output signals from sensor 110 and can determine the contamination level based on those signals. In some embodiments, a separate processor can receive 602 contamination levels from processor 112, or a portion of alerting system 240 can be stored in processor 112, and alerting system 240 can receive 602 the contamination level. Processor 112 can execute the remaining steps in alert sequencing and clearing method 600, or a separate processor can execute the remaining steps.

After receiving 602 the contamination level, alert sequencing and clearing method 600 can include evaluating 604 whether a first alert condition is met. In some embodiments, the first alert condition can be met when the contamination level is outside a predetermined range of contamination levels. In some embodiments, the predetermined range can be between 0 PPM of water and 15 PPM of water.

In some embodiments, the predetermined range can be between 0 PPM of water and 5 PPM of water, or 0 PPM of water and 10 PPM of water, or 0 PPM of water and 20 PPM of water, or 0 PPM of water and 50 PPM of water. In some embodiments, the predetermined range can be between 0 PPM and 15 PPM of DEF, SAF, Avgas, 100 LL, Jet-A, etc. In some embodiments, the predetermined range can be between 0 PPM and 5 PPM, or 0 PPM and 10 PPM, or 0 PPM and 15 PPM, or 0 PPM and 20 PPM of DEF, SAF, Avgas, 100 LL, Jet-A, etc.

In some embodiments, the first alert condition can be met when the contamination level is outside a predetermined range of contamination levels for a predetermined time period, for example, more than 5 seconds or more than 10 seconds. In some embodiments, the predetermined time period can be between 1 and 20 seconds. For example, alert sequencing and clearing method 600 can evaluate 604 that the first alert condition is met when processor 112 receives 602 a contamination level outside a range between 0 PPM of water and 10 PPM of water for five consecutive seconds. In some embodiments, the first alerting condition can be met when alerting system 240 receives 602 a predetermined number of contamination levels outside a predetermined range. In some embodiments, the predetermined number of contamination levels can be between 1 and 10 contamination levels per epoch. For example, processor 112 can receive 602 five output signals from sensor 110 per second, and can determine five contamination levels. Alert determination system 242 can evaluate 604 that the first alerting condition is met because alerting system 240 received 602 five contamination levels outside a predetermined range of contamination levels. Other time periods, contamination ranges, and/or number of contamination levels can be used. The alert conditions discussed herein can mitigate potential false alerts while timely alerting a flight or ground crew of contaminated fuel.

If alert sequencing and clearing method 600 evaluates 604 that the first alert condition is not met, alert sequencing and clearing method 600 can restart and continue to receive 602 contamination levels. If alert sequencing and clearing method 600 evaluates 604 that the first alert condition is met, alert sequencing and clearing method 600 can include delivering 606 a first alert. As discussed, alerting system 240 can deliver a visual and/or aural alert to a flight or ground crew.

Alert sequencing and clearing method 600 can include evaluating 608 whether a first alert clearing condition is met. In some embodiments, the first alert clearing condition is met when a flight crew commands alerting system 240 to clear the alert by, for example, pressing a button that is part of pilot input system 248 (e.g., push-button or touch screen). In some embodiments, at least a part of pilot input system 248 can be integrated with display system 244. For example, pilot input system 248 can include a pop-up notification on display system 244 that the flight crew can select to clear an alert. In some embodiments, the first alert clearing condition is met when alerting system 240 receives a predetermined number of contamination levels within a predetermined range of contaminations levels, indicating that aircraft 102 is not currently receiving contaminated fuel.

The alert clearing condition can depend on changes in fuel contamination levels. For example, if alerting determination system 242 evaluated 604 that the first alert condition was met based on a single contamination level in the first second of fueling, and then evaluates 604 that the first alert condition is not met for the next ten seconds, alerting system 240 can evaluate 608 that the first alert clearing condition is met. The initial alert may have been a false alert, or may have been associated with a negligible amount of contamination that would not impact engine performance. As another example, if alert determination system 242 evaluates 604 that the first alert condition is met for the first fifteen seconds of fueling, alerting system 240 can evaluate 608 that the alert clearing condition is met only if the flight crew clears the alert. For example, if fuel line 118 connects to a lower portion of fuel source 106, and fuel source 106 contains water and jet fuel, the water may enter aircraft fuel tank 104 before the jet fuel because water is denser than jet fuel. If alerting system 240 automatically clears the alert after receiving uncontaminated fuel for a predetermined period, the flight crew may not be aware that contaminated fuel entered aircraft fuel tank 104 first. Maintaining the alert until the flight crew clears it can ensure the flight crew sees the alert.

In some embodiments, if alerting system 240 evaluates 608 first alerting clearing condition is met, alerting system 240 can clear 610 the alert. For example, alerting system 240 can update display system 244 to no longer display a text alert, or can stop commanding audio system 246 to deliver aural alerts. After clearing 610 the alert, alert sequencing and clearing method 600 can restart by continuing to receive 602 contamination levels.

If alerting system 240 evaluates 608 that the first alert clearing condition is not met, alert sequencing and clearing method 600 can include evaluating 612 if a second alert condition is met. If alerting system 240 evaluates 612 that the second alert condition is not met, alert sequencing and clearing method 600 can restart to continue receiving 602 contamination levels. If alerting system 240 evaluates 612 that the second alert condition is met, alerting system 240 can deliver 614 a second alert. In some embodiments, the second alert condition can be the same as the first alert condition. In some embodiments, the second alert condition is different from the first alert condition. For example, alerting system 240 can deliver 606 a first alert if the contamination level is outside a predetermined range for a first predetermined time period, and alerting system 240 can deliver 614 a second alert if the contamination level is outside the predetermined range for a second predetermined time period. As another example, alerting system 240 can deliver 606 a first alert if the contamination level is outside a first predetermined range, and alerting system 240 can deliver 614 a second alert if the contamination level is outside a second predetermined range that is different from the first predetermined ranged. In some embodiments, the first alert is a different type of alert than the second alert. For example, the first alert can be a visual alert on display system 244 and the second alert can be an aural alert issued through audio system 246. Sequencing a first alert and a second alert based on different time periods or predetermined ranges of contamination levels can alert the flight crew of varying severity of contaminated fuel, and can alert the flight crew without unnecessarily interfering with other pre-flight operations, or causing panic.

In some embodiments, alert sequencing and clearing method 600 can include evaluating 616 if the second alert clearing condition is met, and clearing 610 the second alert if the second alert clearing condition is met. In some embodiments, the second alert clearing condition can be satisfied in the same manner as the first alert clearing condition. For example, the first and second alert clearing condition can be met when the flight crew presses a button that is part of pilot input system 248. In other embodiments, the second alerting clearing condition can be met in a different manner than the first alert clearing condition. For example, if the first alert is associated with a lower contamination level than the second alert, alerting system 240 can evaluate 608 that the first alert clearing condition is met when contamination levels are within a predetermined range for a predetermined period. By contrast, alerting system 240 can evaluate 616 that the second alert clearing condition is met when the flight crew presses a button that is part of the pilot input system 248. Distinct alert clearing conditions can help ensure the flight crew responds to the alerts of contaminated fuel, without unnecessarily interfering with preflight operations if the contamination is insignificant.

Figure 8:
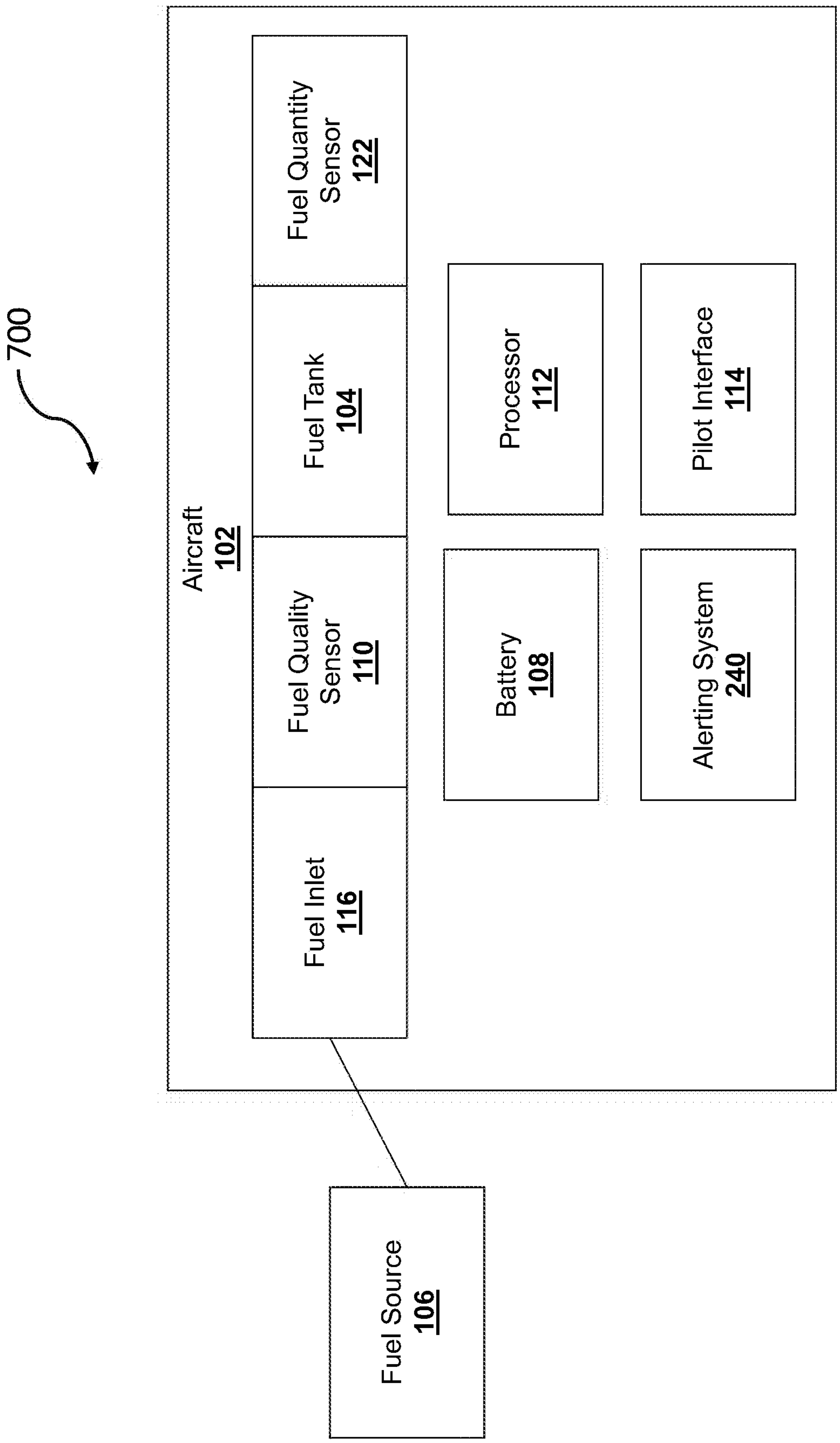
FIG. 8 illustrates a system block diagram of a relative fuel quality monitoring and alerting system according to an embodiment.

In some embodiments, a fuel quality monitoring and alerting system 700 can be configured to alert a flight crew to poor fuel quality based on the incoming fuel quality and the amount of fuel in fuel tank 104. In some embodiments, as shown for example in FIG. 8, fuel quality monitoring and alerting system 700 can include a fuel quantity sensor 122 configured to output a signal corresponding to the amount of fuel in fuel tank 104. In some embodiments, for example, aircraft 102 can include a Fuel Quantity Indication System (FQIS) that includes fuel quantity sensor 122. In some embodiments, fuel quantity sensor 122 can be configured to output a signal corresponding to the usable fuel in fuel tank 104. Usable fuel is the fuel that can be reliably delivered to engine 120 across normal operating conditions (e.g., accounting for aircraft 102 orientation, pump locations, etc.) and/or the total amount of fuel in the fuel tank 104. Alerting based on incoming fuel quality and the amount of fuel in fuel tank 104 can, for example, mitigate nuisance alerts (e.g., where contaminated fuel accounts for an insignificant portion of the fuel in fuel tank 104 and does not create a safety concern).

In some embodiments, processor 112 is configured to determine a relative contamination level of fuel in fuel tank 104 based on the amount of fuel in fuel tank 104 and the contamination level of incoming fuel. In some embodiments, the relative contamination level is the amount (e.g., gallons, liters, quarts, etc.) of contaminated fuel (e.g., contamination level outside a range, as discussed above) relative to the amount of fuel (e.g., gallons) in fuel tank 104. In some embodiments, for example, alerting system 240 is configured to deliver an alert to pilot interface 114 if the proportion of contaminated fuel relative to the amount of fuel in fuel tank 104 exceeds 1%. In some embodiments, alerting system 240 is configured to deliver an alert to pilot interface 114 if the proportion of contaminated fuel relative to the amount of fuel in fuel tank 104 is outside a range. In some embodiments, the range is between 0% and 0.5%, 0% and 1%, 0% and 2%, 0% and 5%, 0% and 10%, or 0% and 20%. Processor 112 can determine the relative contamination level of fuel in fuel tank 104 over a period (e.g., 30 seconds). In some embodiments, the period can be between 10 seconds and 20 seconds, between 10 seconds and 30 seconds, between 10 seconds and 60 seconds. In some embodiments, the period can be between 1 minute and 2 minutes, 1 minute and 3 minutes, 1 minute and 4 minutes, 1 minute and 5 minutes, or 1 minute and 10 minutes.

For example, assuming fueling begins with 100 gallons of fuel in fuel tank 104, fueling proceeds for 30 seconds to add 100 gallons of fuel to fuel tank 104, and processor 112 determined one gallon of fuel that entered fuel tank 104 was contaminated, processor 112 can determine that the relative contamination level is 0.5% ([1 contaminated gallon]/[100 initial gallons+100 added gallons]). As another example, processor 112 can determine that there are currently 100 gallons of fuel in fuel tank 104 and that 20 gallons of contaminated fuel entered fuel tank 104 during a period, resulting in a proportion of contaminated fuel equivalent to 20% or a proportion of non-contaminated fuel equivalent to 80%.

These are non-limiting examples and provided for illustrative purposes. Various computational techniques and numerical methods can be used to determine the relative contamination level of fuel in fuel tank 104 without departing from the scope of the present disclosure.

As discussed above, contaminated fuel can be determined based on the amount of a contaminate (e.g., water, incorrect fuel type, etc.). In some embodiments, for example, the relative contamination level corresponds to the amount of fuel (e.g., gallons, liters, quarts, etc.) that entered fuel tank 104 and deviates from a predetermined fuel profile. A predetermined fuel profile can include relative proportions (e.g., percent by weight) of components forming a fuel type (e.g., a fuel type that is appropriate for aircraft 102 and/or engine 120). In some embodiments, the predetermined fuel profile can include a ratio of a first fuel component (e.g., n-paraffins, isoparaffins, naphthenes, aromatics, etc.) to a second fuel component. The ratio can correspond to a fuel type, such as Jet-A, 100 LL, etc.

In some embodiments, processor 112 can classify the incoming fuel as a fuel type and can determine if the fuel type entering fuel tank 104 is compatible with aircraft 102 and/or engine 120. If, for example, SAF is entering aircraft fuel tank 104, processor 112 can classify the incoming fuel as SAF and can determine whether SAF is or is not compatible (e.g., based on the intended fuel type being JET-A) and/or can determine that the fuel profile of the incoming fuel deviates from a fuel profile (e.g., a fuel profile corresponding to Jet-A). In some embodiments, alerting system 240 can be configured to deliver an alert based on the fuel type entering fuel tank 104 and the amount of fuel in fuel tank 104 (e.g., relative contamination level).

Processor 112 can be configured to classify the incoming fuel type based on one or more signals output by sensors (e.g., sensor 110) and corresponding to, for example, capacitance, dielectric constant, UV-Vis, density, turbidity, etc.) In some embodiments, processor 112 can be configured to classify the incoming fuel type based on one or more measurement techniques (e.g., measuring the resistance of the fluid, for example, as it passes through fuel inlet 116, measuring light transmitted through the fluid at a predetermined angle, measuring the pressure of a volume of the fluid, etc.)

The embodiments disclosed herein can include a relative fuel quality monitoring and alerting method 800 that balances goals of alerting the flight crew to contaminated fuel and mitigating nuisance alerts that can cause undesirable operational delays.

Figure 9:
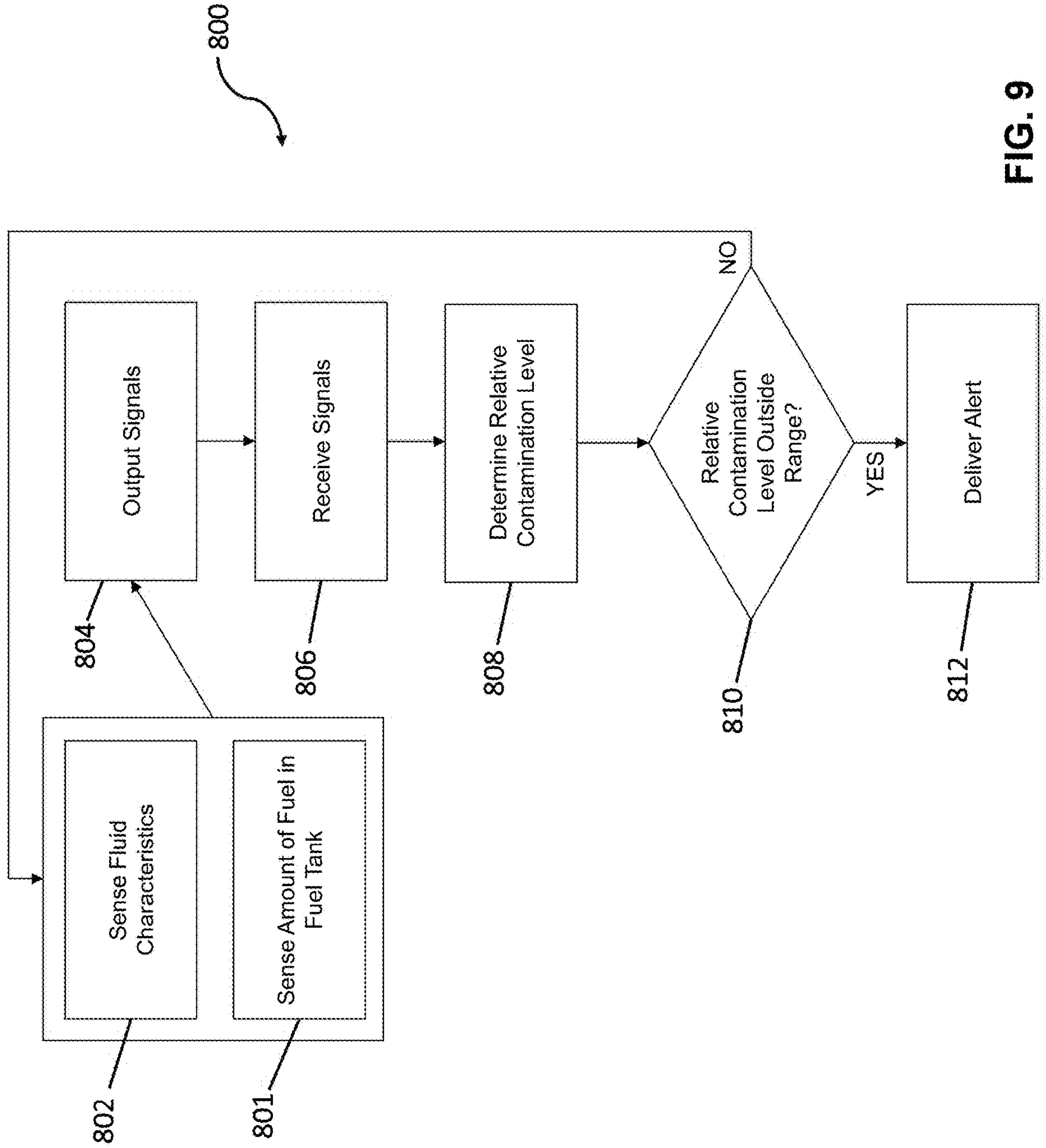
FIG. 9 is a flowchart of a relative fuel quality monitoring and alerting method according to an embodiment.

Referring to FIG. 9, relative fuel quality monitoring and alerting method 800 can include sensing 801 the amount of fuel in fuel tank 104 and sensing 802 fluid characteristics (discussed above) of incoming fuel. In some embodiments, method 800 can include outputting 804 (e.g., by fuel quality sensor 110 and/or fuel quantity sensor 122) signals corresponding to the contamination level of fuel entering fuel tank 104 and the amount of fuel in fuel tank 104. In some embodiments, method 800 can include receiving 806 (e.g., by processor 112) signals corresponding to the contamination level of fuel entering fuel tank 104 and/or the amount of fuel in fuel tank 104.

In some embodiments, processor 112 can be configured to determine 808 the relative contamination level of fuel in fuel tank 104 based on the contamination level of fuel entering fuel tank 104 and the amount of fuel in fuel tank 104. As discussed above, processor 112 can be configured to determine whether fuel is contaminated based on an amount of specific contaminate (e.g., water, surfactants, etc.) and/or based on the fuel type entering fuel tank 104.

In some embodiments, method 800 can include determining 810 (e.g., by processor 112) if the relative contamination level is outside a range. In some embodiments, the range is between 0% and 1% (e.g., the amount of contaminated fuel that entered fuel tank 104 during fueling account for between 0% and 1% of the fuel in fuel tank 104). In some embodiments, the range is between 0% and 0.5%. In some embodiments, the range is between 0% and 0.1%. In some embodiments, the range is between 0% and 1%, 0% and 2%, 0% and 5%, 0% and 10%, or 0% and 20%.

In some embodiments, if the relative contamination level is outside the range, method 800 can include delivering 812 (e.g., by alerting system 240) an alert to pilot interface 114. In some embodiments, if the relative contamination level is not outside the range, method 800 can continue sensing 801 the amount of fuel in fuel tank 104 and sensing 802 fluid characteristics of the fuel entering fuel tank 104.

In some embodiments, the range (e.g., to evaluate the contamination level) is an independent constant range (e.g., 0% to 1%). In some embodiments, the range is variable. In some embodiments, for example, the range can be based on the type of fuel entering fuel tank 104, the type of fuel source 106, the location of aircraft 102, and/or historical data (e.g., prior alerting conditions). In some embodiments, for example, processor 112 can receive a signal (e.g., from a memory storage device, another processor) corresponding to fuel source 106 (e.g., fuel truck, fuel hydrant dispenser, gravity-feed, pressure-based, etc.) and the range can correspond (e.g., database stored on processor 112, cloud computing device, etc.) to fuel source 106. For example, the predetermined range can be between 0% and 1% for a first fuel source 106 (e.g., fuel truck) and between 0% and 2% for a second fuel source 106 (e.g., hydrant dispenser). Adjusting the range based on fuel source 106 can mitigate nuisance alerts to reduce unnecessary operational delays. For example, a wider range can mitigate nuisance alerts caused by a faulty fuel quality sensor 110 indicating poor fuel quality for a fuel source 106 known to consistently provide high quality fuel. At the same time, a tight range can minimize tolerance for poor fuel where fuel source 106 is known to provide relatively (e.g., to industry standards) low quality fuel.

As another example, in some embodiments the range can be based on the type of fuel entering fuel tank 104. For example, a tighter range can correspond to fuel types known to be highly hazardous if mixed into fuel tank 104 (e.g., mixing SAF with Jet-A). A wider range can correspond to fuel types that are acceptable, but not preferable (e.g., mixing 100 LL into aircraft 102 that is supposed to use JET-A). As discussed above, adjusting the range based on fuel type can mitigate nuisance alerts to reduce unnecessary operational delays.

In some embodiments, processor 112 can be configured to receive a signal corresponding to aircraft's 102 location (e.g., GPS coordinates) and the range can correspond to aircraft's 102 location. For example, the range can be between 0% and 1% at a first location (e.g., an area known to have poor fuel), and can be between 0% and 2% at a second location (e.g., an area known to have high quality fuel). Adjusting the range based on aircraft's 102 location can mitigate nuisance alerts caused by a faulty fuel quality sensor 110 in, for example, locations known to have high quality fuel, while also maintaining tight thresholds in locations known to have poor fuel.

In some embodiments, the range can be manually adjusted (e.g., by updating a look up table/database, updating software, etc.). In some embodiments, the range can be dynamically adjusted by, for example, an artificial intelligence-based algorithm (e.g., utilizing machine learning) based on data (e.g., alerts, contamination levels, etc.) from one or more aircraft 102. In some embodiments, for example, aircraft 102 can store contamination levels, alerts, location, fuel source 106, fuel type, etc. in memory. If a particular aircraft 102 begins routinely operating out of an airport that introduces a new fuel type (e.g., SAF) as a fueling option, the range can be dynamically adjusted (e.g., tightened) after repeated alerts at that airport.

Figure 10:
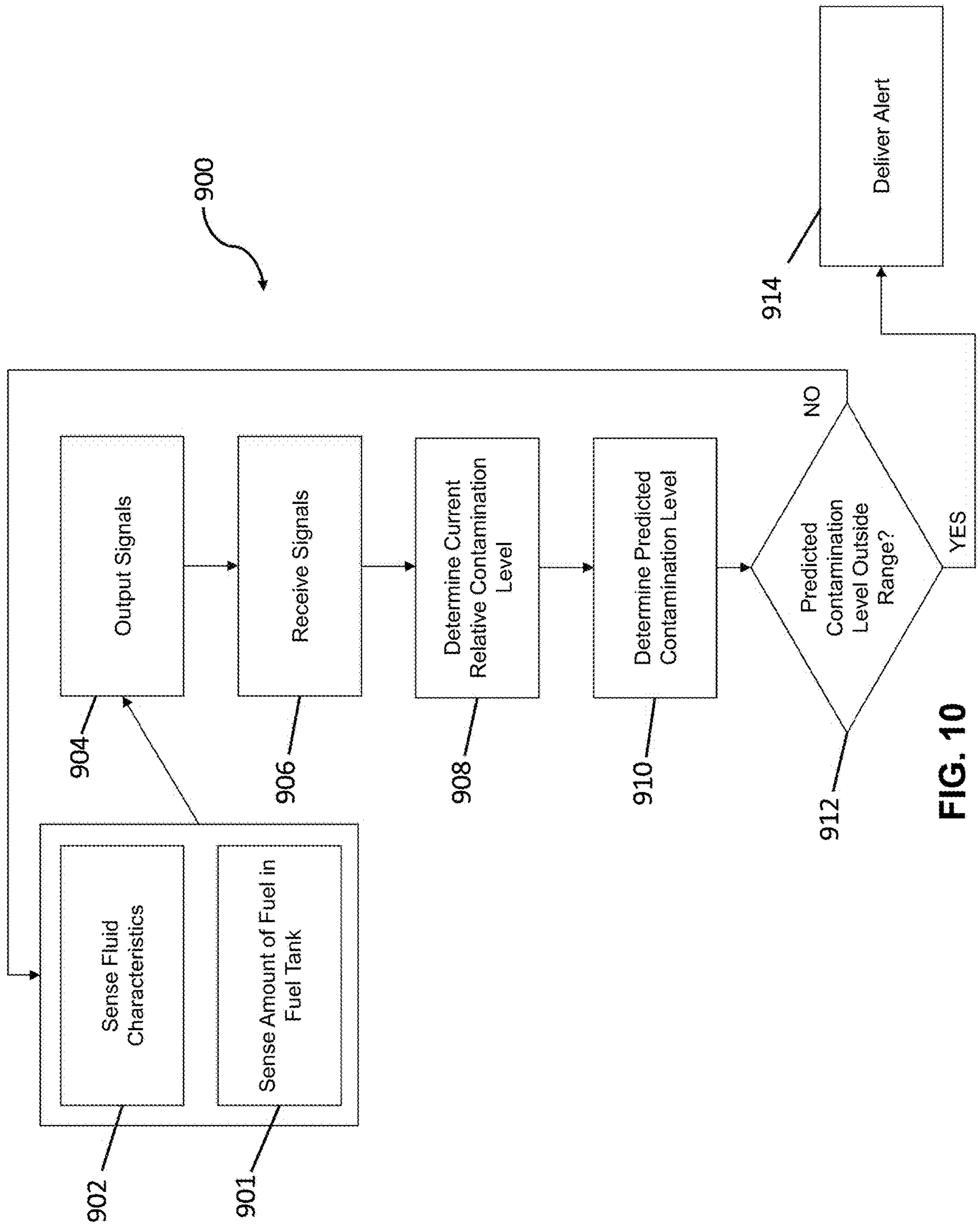
FIG. 10 is a flowchart of a predictive fuel quality monitoring and alerting method according to an embodiment.

In some embodiments, as shown for example in FIG. 10, the embodiments disclosed herein can include a predictive alerting method 900. Predictive alerting can, for example, complement alerts based on the contamination level of incoming fuel and/or the amount of fuel in fuel tank 104. Predictive alerting can provide flight crews with heightened situational awareness to improve decision making.

In some embodiments, method 900 can include sensing 901 the amount of fuel in fuel tank 104 and sensing 902 one or more fluid characteristics of, for example, fuel entering fuel tank 104. In some embodiments, method 900 can include outputting 904 (e.g., by fuel quality sensor 110 and/or fuel quantity sensor 122) signals corresponding to the amount of fuel in fuel tank 104 and/or the contamination level of fuel entering fuel tank 104. In some embodiments, method 900 can include receiving 906 (e.g., by processor 112) signals corresponding to the quantity of fuel in fuel tank 104 and/or the contamination level of fuel entering fuel tank 104.

In some embodiments, processor 112 can be configured to determine 908 a current relative contamination level of fuel in fuel tank 104, as discussed above relative to FIGS. 8-9. In some embodiments, processor 112 can be configured to determine 910 a predicted contamination level of fuel inside fuel tank 104. If, for example, processor 112 determines 912 that the predicted contamination level is outside the predetermined range, alerting system 240 can deliver 914 an alert to pilot interface 114. If processor 112 determines 912 that the predicted contamination level is not outside the predetermined range, method 900 can continue to sense 901 the amount of fuel in fuel tank 104 and sense 902 the fluid characteristics of the fuel entering fuel tank 104.

In some embodiments, processor 112 can be configured to determine a predicted contamination level (e.g., relative contamination level) of fuel inside fuel tank 104 after a predetermined period (e.g., between 10 and 60 seconds). In some embodiments, processor 112 can be configured to determine a predicted contamination level based on at least one of a fuel flow rate, a period, an amount of fuel, the current amount of fuel in fuel tank 104, and/or a capacity of the fuel tank 104. In some embodiments, the amount of fuel corresponds to the amount of fuel expected to be in fuel tank 104 after fueling is complete. For example, in some embodiments, the amount of fuel is based on the amount of fuel in fuel tank 104 and a flight plan (e.g., input to pilot input system 248, such as on an MCDU or EFB). In some embodiments, processor 112 can be configured to determine the amount of fuel that will be in fuel tank 104 after fueling is complete based on the flight plan (e.g., trip distance) and an average fuel burn.

In some embodiments, processor 112 can be configured to determine a predicted relative contamination level based on the current relative contamination level (e.g., 0%), the amount of fuel in fuel tank (e.g., 3,000 gallons), the contamination level of fuel entering fuel tank 104 (e.g., 20 PPM), the fuel flow rate (e.g., 300 gallons per minute), and/or a period (e.g., 5 minutes). In this example, processor 112 can determine that if the current fuel entering fuel tank 104 continues flowing at 300 gallons per minute for 5 minutes, there will be 4,500 gallons of fuel in fuel tank 104, with 1,500 gallons having contamination levels outside a range (e.g., between 0 and 15 PPM). In this example, processor 112 can determine the predicted relative contamination level is approximately 33%.

This is a non-limiting example and is provided for illustrative purposes. Processor 112 can be configured to execute a variety of predictive and/or estimation algorithms without departing from the scope of the present disclosure. In some embodiments, for example, processor 112 can be configured to execute algorithms incorporating machine-learning, neural networks, regression models, decision trees, classification models, time series models, clustering models, support vector machines, random forests, etc.

A flight crew in-the-loop fuel quality monitoring system can supply flight crews with situational awareness to balance operational efficiency and safety. For example, as discussed above, in some embodiments alerting system 240 can be configured to deliver an alert to pilot interface 114 until the alert is extinguished by input on pilot input system 248. Maintaining the alert until it is extinguished by, for example, the flight crew, mitigates the possibility that a defect in fuel quality sensor 110 and/or fuel quantity sensor 122 contributes to operational delays (e.g., inappropriate fuel shut off increasing fueling time).

In some embodiments, the systems and methods disclosed herein incorporate flight crew input (e.g., via pilot input system 248) and/or automated fuel shut-off to prevent fuel from entering fuel tank 104. In some embodiments, a combination of flight crew input and automated fuel shut-off can provide flight crews with sufficient authority to exercise aeronautical decision-making while also supplying an additional safety layer if, for example, the flight crew is not attentive, the incoming fuel contamination level is excessively high (e.g., between 0 PPM and 30 PPM as compared to a baseline range of between 0 PPM and 15 PPM), the predicted contamination level is excessively high (e.g., between 0% and 10% as opposed to a baseline range between 0% and 1%), and/or the incoming fuel contamination level is outside a range (e.g., between 0 PPM and 15 PPM) for a long period (e.g., 60 seconds as opposed to a baseline period of 10 seconds).

Figure 11:
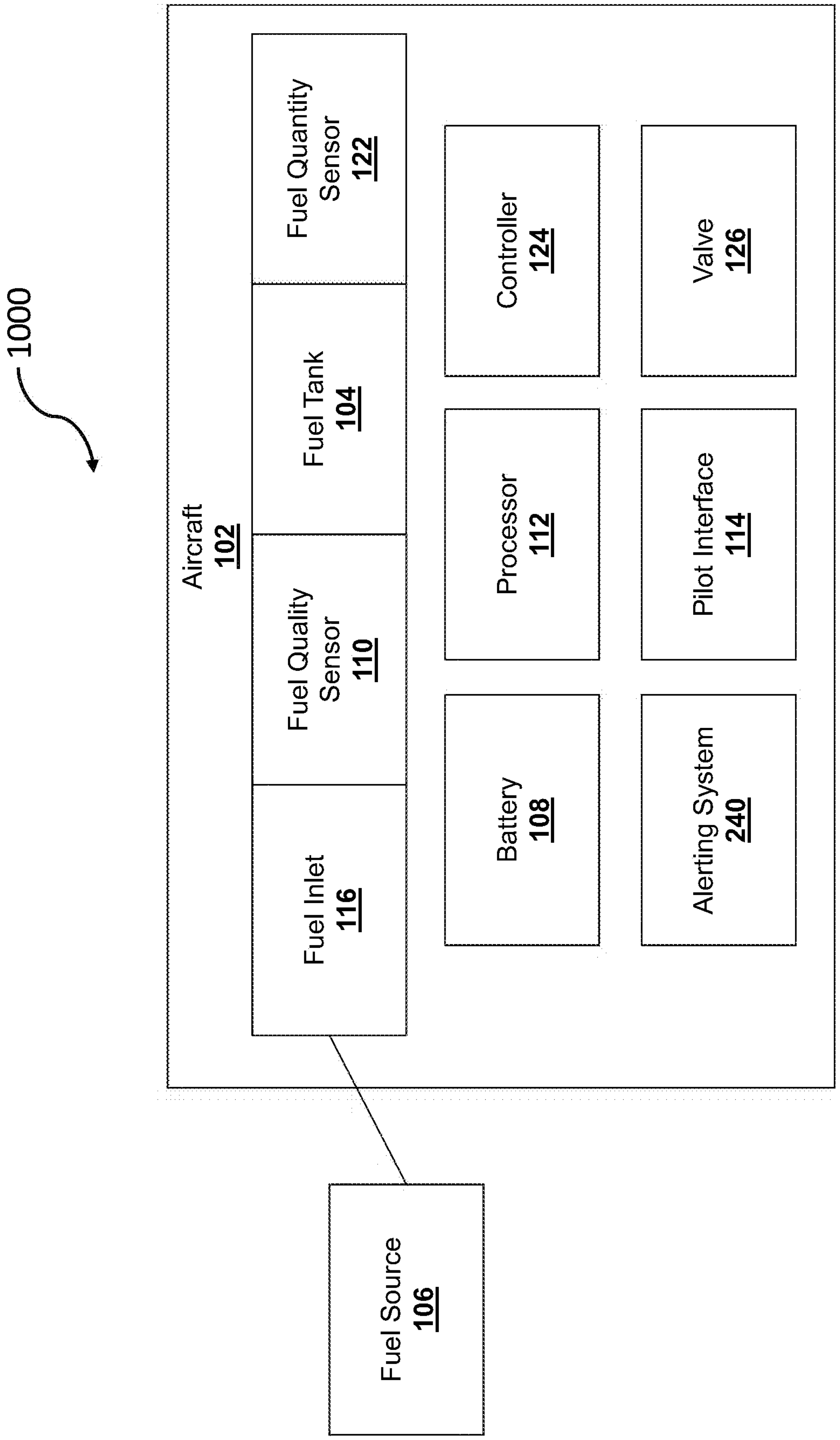
FIG. 11 illustrates a system block diagram of a fuel quality monitoring, alerting, and shut-off system with an aircraft including a shut-off valve, according to an embodiment.
Figure 12:
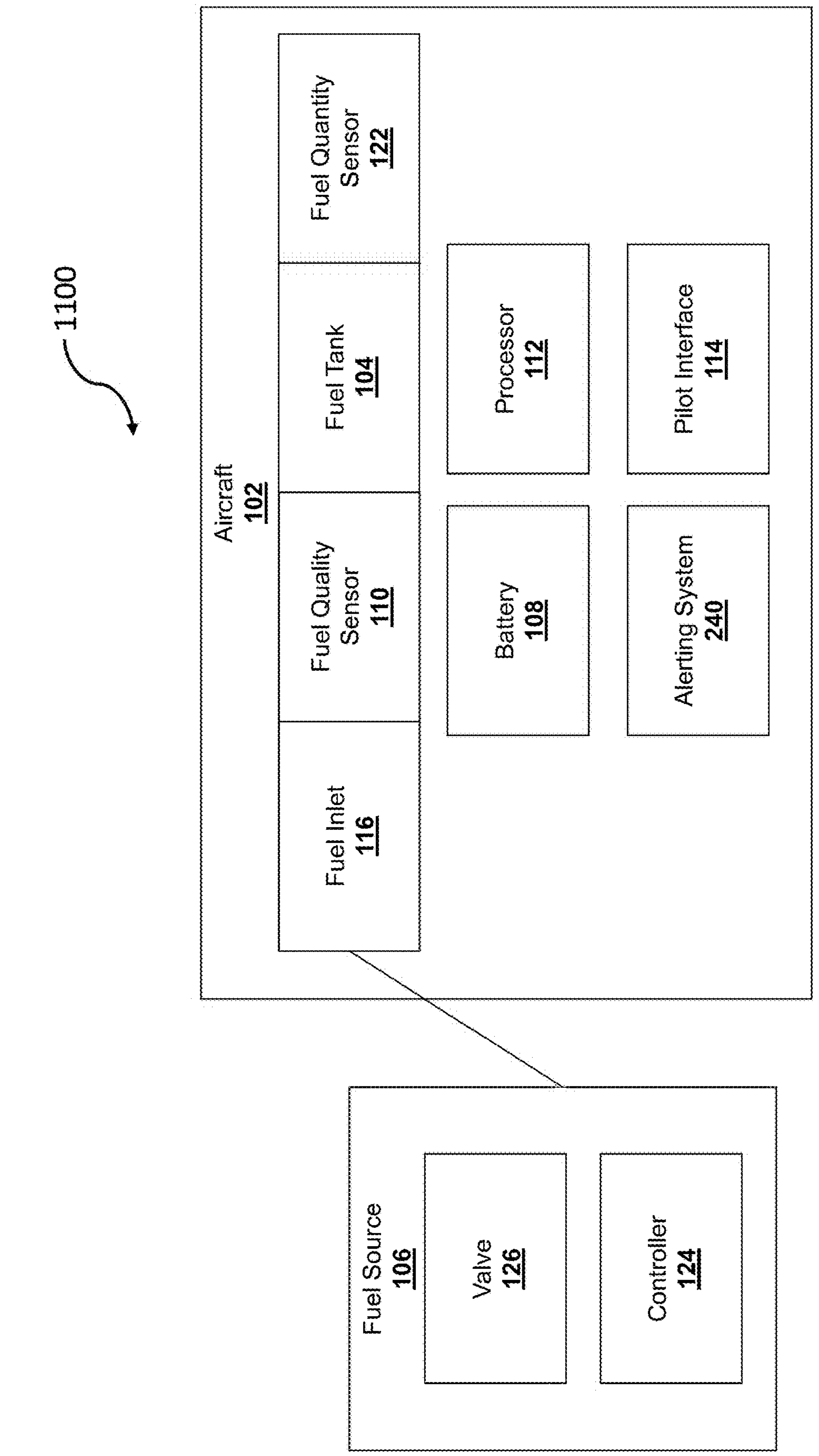
FIG. 12 illustrates a system block diagram of a fuel quality monitoring, alerting, and shut-off system with a fuel source including a shut-off valve, according to an embodiment.

In some embodiments, as shown for example in FIG. 11, a fuel quality monitoring and shut-off system 1000 includes a controller 124. In some embodiments, as shown for example in FIG. 11, aircraft 102 includes controller 124. In some embodiments, as shown for example in FIG. 12, a fuel quality monitoring and shut-off system 1100 include controller 124 external to aircraft 102 (e.g., fuel source 106).

In some embodiments, controller 124 can be configured to prevent fuel from entering fuel tank 104 (e.g., by actuating a valve) if, for example, one or more fuel shut-off conditions are satisfied. In some embodiments, the fuel shut-off condition can be based on, for example, input via pilot interface 114, the contamination level of fuel entering fuel tank 104, the relative contamination level of fuel in fuel tank 104, and/or the predicted contamination level of fuel in fuel tank 104.

In some embodiments, as shown for example in FIG. 11, aircraft fuel quality monitoring system 1100 can include a valve 126 configured to prevent fuel from entering fuel tank 104. In some embodiments, controller 124 is configured to actuate valve 126 to prevent fuel from entering fuel tank 104 if a fuel-shut off condition is satisfied. In some embodiments, as shown for example in FIG. 11, valve 126 is disposed on or inside aircraft 102 (e.g., at fuel inlet 116). In some embodiments, as shown for example in FIG. 12, fuel source 106 includes valve 126. In some embodiments, aircraft 102 includes a valve 126 and fuel source 106 includes a valve 126 configured to prevent fuel from entering fuel tank 104. In some embodiments, aircraft 102 includes valve 126 and fuel source 106 includes controller 124. In some embodiments, fuel source 106 includes valve 126 and aircraft 102 includes controller 124.

In some embodiments, alerting system 240 can be configured to deliver an alert if the contamination level of fuel entering fuel tank 104 is outside a first range (e.g., 0 PPM to 15 PPM) and controller 124 can be configured to prevent fuel from flowing into fuel tank 104 if the contamination level of fuel entering fuel tank 104 is outside a second range (e.g., 0 PPM to 30 PPM). In some embodiments, alerting system 240 can be configured to deliver an alert if the relative contamination level of fuel in fuel tank 104 is outside a first range (e.g., 0% to 1%) and controller 124 can be configured to prevent fuel from entering fuel tank 104 if the relative contamination level is outside a second range (e.g., 0% to 10%). In some embodiments, alerting system 240 can be configured to deliver an alert if the predicted contamination level of fuel in fuel tank 104 is outside a first range (e.g., 0% to 1%) and controller 124 can be configured to prevent fuel from entering fuel tank 104 if the predicted contamination level is outside a second range (e.g., 0% to 10%). Alerting the flight crew before stopping fuel flow under certain conditions and automatically stopping fuel flow under, for example, more severe conditions (e.g., greater contamination levels) can prevent unnecessary operational delays. For example, if the fuel contamination (e.g., incoming, relative, predicted) is acceptable to the crew, the crew can allow fueling to continue without sumping the tanks and restarting. However, if a fuel shut-off condition is satisfied (e.g., severe contamination level indicates high probability that fuel is unsafe), automatically stopping fueling can reduce time spent sumping the tanks.

As discussed above, the contamination levels disclosed herein can correspond to water, particulates, etc. and incorrect fuel types. For example, as discussed above, processor 112 can be configured to classify the fuel entering fuel tank 104 as a fuel type (e.g., based on the fuel profile), and can determine the relative proportion of a fuel type (e.g., an appropriate fuel type for aircraft 102) in fuel tank 104, and a predicted proportion of a fuel type (e.g., an appropriate fuel type for aircraft 102). In some embodiments, controller 124 can be configured to prevent fuel from entering fuel tank 104 based on the fuel type entering fuel tank 104.

In some embodiments, for example, controller 124 can be configured to prevent fuel from entering fuel tank 104 if the predicted proportion of a first fuel (e.g., the appropriate fuel for aircraft 102) is below a minimum proportion (e.g., 99% (0.99) or 95% (0.95)). In some embodiments, the minimum proportion is between approximately 80% and 99.9%, 85% and 99.9%, 90% and 99.9%, 95% and 99.9%, 98% and 99.9% or 99% and 99.9%. In some embodiments, for example, controller 124 can be configured to prevent fuel from entering fuel tank 104 if the predicted proportion of a first fuel inside fuel tank 104 is below a minimum proportion for a consecutive number of epochs (e.g., 10 consecutive contamination levels). In some embodiments, for example, controller 124 can be configured to prevent fuel from entering fuel tank 104 if the predicted proportion of a first fuel inside fuel tank 104 is below a minimum proportion and controller 124 receives input (e.g., via pilot input system 248). Flight crew input to stop fueling can reduce operational delays introduced by, for example, a faulty fuel quality sensor 110. For example, after an initial alert, the flight crew can stop fueling, sump fuel tank 104, and check fuel quality using an independent source (e.g., manual sample). If, after manually checking the fuel and/or fuel source 106, the flight crew can opt to proceed with fueling if alerting system 240 again delivers an alert during refueling.

In some embodiments, alerting system 240 can be configured to deliver an alert (e.g., to pilot interface 114) if controller 124 prevents fuel from entering fuel tank 104 (e.g., by actuating valve 126). Alerting the flight crew that controller 124 prevented fuel from entering fuel tank 104 provides situational awareness where, for example, the flight crew stepped away during fueling, did not observe an alert from alerting system 240, the fuel-shut off condition (e.g., incoming fuel contamination level outside 0 PPM to 30 PPM) was satisfied as fueling started, etc.

Figure 13:
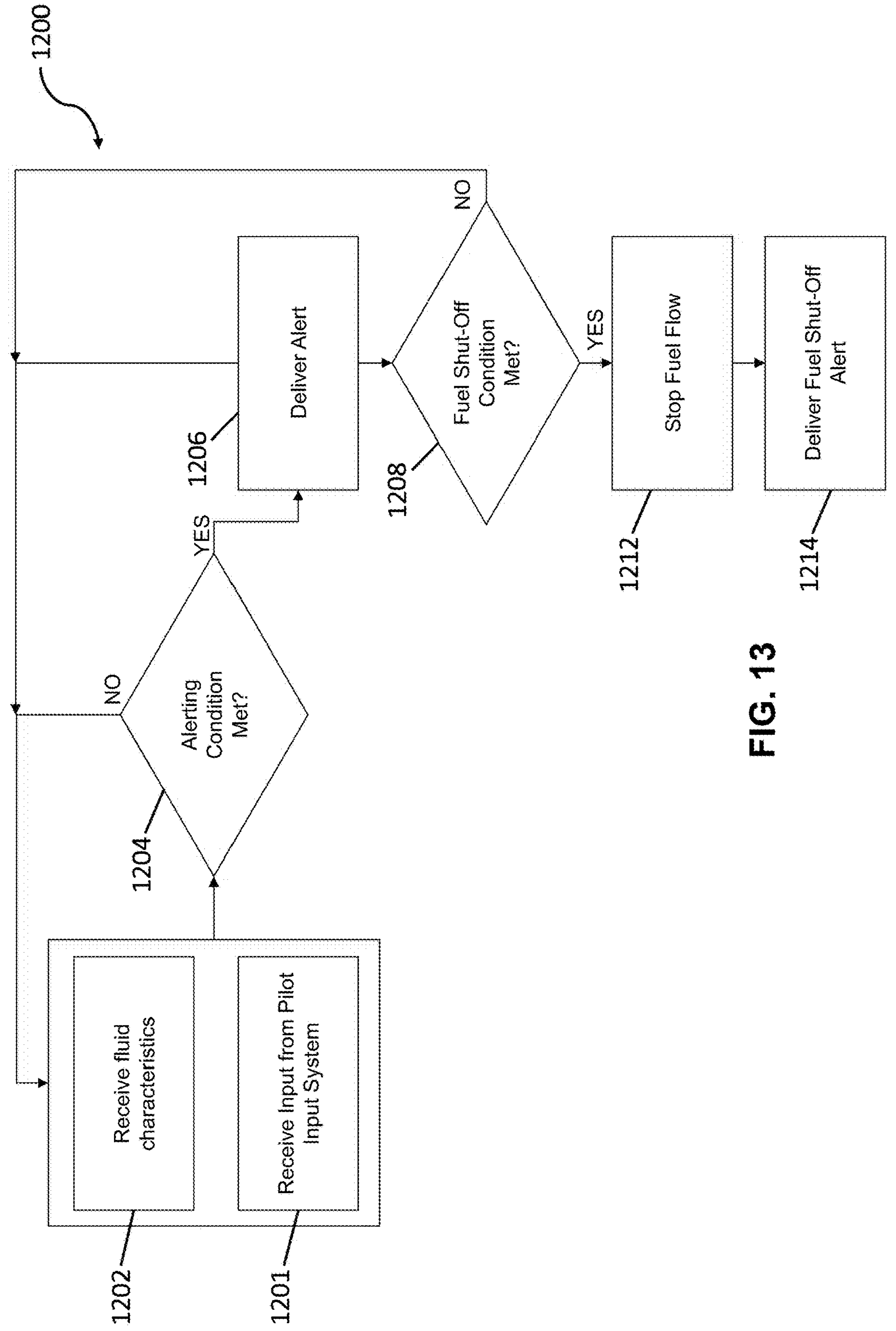
FIG. 13 is a flowchart of a fuel quality monitoring, alerting, and shut-off method according to an embodiment.

FIG. 13 illustrates a fuel quality monitoring and shut-off method 1200. In some embodiments, method 1200 includes receiving 1201 (e.g., by processor 112) input from pilot input system 248 and/or receiving 1202 (e.g., by processor 112) fluid characteristics from, for example, fuel quality sensor 110 and/or fuel quantity sensor 122. As discussed above, processor 112 can be configured to determine the quantity of fuel in fuel tank 104, the contamination level of fuel entering fuel tank 104, the relative contamination level of fuel in fuel tank 104, and/or the predicted contamination level of fuel in fuel tank 104.

In some embodiments, method 1200 can include determining 1204 whether an alerting condition is met. As discussed above, the alerting condition can be met, for example, if the contamination level of fuel entering fuel tank 104 is outside a range, the relative contamination level of fuel in fuel tank 104 is outside a range, and/or the predicted contamination level of fuel in fuel tank 104 is outside a range.

If the alerting condition is met, alerting system 240 can deliver 1206 an alert (e.g., to pilot interface 114). If the alerting condition is not met, method 1200 can continue to receive 1201 input from pilot input system 248 and/or receive 1202 fluid characteristics from fuel quality sensor 110 and/or fuel quantity sensor 122.

In some embodiments, as shown for example in FIG. 13, method 1200 can include determining 1208 whether a fuel shut-off condition is met. As discussed above, a fuel-shut condition can be met based on the contamination level of fuel entering fuel tank 104, the relative contamination level of fuel in fuel tank 104, the predicted contamination level of fuel in fuel tank 104, and/or input from pilot input system 248. In some embodiments, if processor 112 determines 1208 that a fuel shut-off condition is met, controller 124 can stop 1212 fuel from entering fuel tank 104 (e.g., by actuating valve 126). If processor 112 determines 1208 that a fuel shut-off condition is not met, method 1200 can continue to receive 1201 input from pilot input system 248 and/or receive 1202 fluid characteristics.

As discussed above, if, for example, alerting system 240 can be configured to continue delivering 1206 the alert (e.g., remain on display system 244 and/or continue outputting audio through audio system 246) until the alert is extinguished by input on pilot input system 248. For example, if processor 112 determines 1204 that an alerting condition is met, but determines 1208 that a fuel shut-off condition is not met, alerting system 240 can continue delivering 1206 an alert until extinguished by input on pilot input system 248, but controller 124 will not stop 1212 fuel from entering fuel tank 104.

In some embodiments, as shown for example in FIG. 13, method 1200 can include delivering 1214 a fuel shut-off alert (e.g., to pilot interface 114) if, for example, controller 124 stops 1212 fuel from entering fuel tank 104. As discussed above, delivering 1214 a fuel shut-off alert provides flight crews with situational awareness where, for example, the flight crew stepped away during fueling, did not observe an alert from alerting system 240, the fuel-shut off condition (e.g., incoming fuel contamination level outside 0 PPM to 30 PPM) was satisfied as fueling started, etc.

Figure 14:
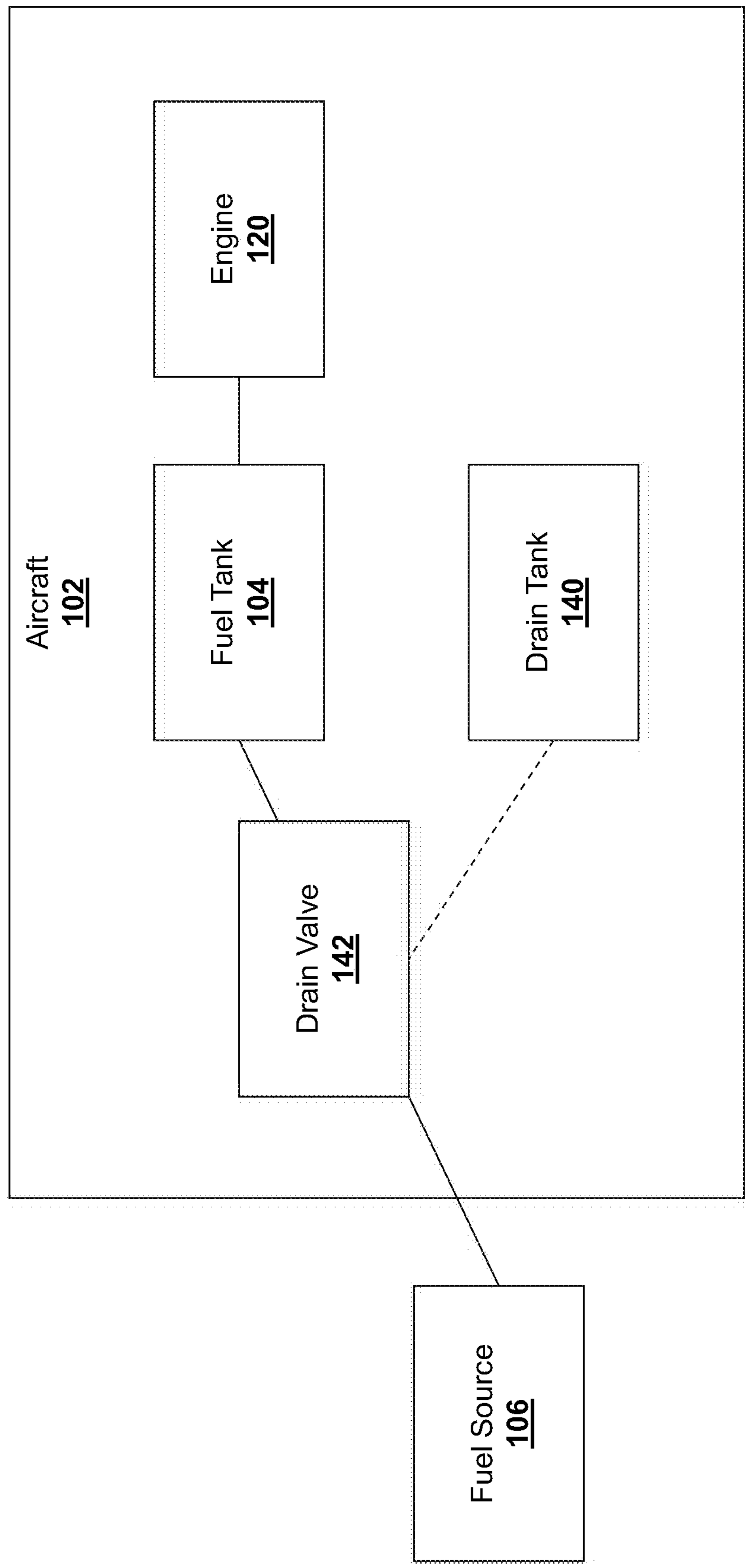
FIG. 14 illustrates a system block diagram of a fuel quality monitoring system with a drain valve and drain tank, according to an embodiment.

In some embodiments, the fuel quality monitoring and alerting systems disclosed herein can be configured to redirect incoming fuel if, for example, processor 112 determines that the incoming fuel is contaminated. In some embodiments, as shown for example in FIG. 14, aircraft 102 can include fuel tank 104 and drain tank 140. In some embodiments, fuel tank 104 can be configured to receive incoming fuel and supply fuel to engine 120, and drain tank 140 can be configured to receive contaminated fuel. In some embodiments, for example, aircraft 102 can include a drain valve 142 configured to actuate if processor 112 determines that the incoming fuel is contaminated. In some embodiments, drain valve 142 is configured to actuate to redirect incoming fuel to drain tank 140 to prevent contaminated fuel from entering fuel tank 104.

In some embodiments, aircraft 102 can include internal fuel line flushing systems configured to clear the internal fuel lines if, for example, processor 112 determines that the incoming fuel is contaminated. In some embodiments, aircraft 102 can include a sump system configured to sump the fuel tanks if, for example, processor 112 determines that the incoming fuel is contaminated.

The embodiments disclosed herein can further comprise memory configured to store information associated with an alert. The information associated with an alert can include the time of the alert, an identifier indicating the type of alert (e.g., advisory or warning, and first or second alert), an identifier indicating the first alert condition, an identifier indicating the second alert condition, output signals 111, contamination level(s), aircraft type, or any other parameter relevant to the alert. The embodiments disclosed herein can include storing information associated with an alert in a database (e.g., stored on aircraft 102, cloud-based storage, blockchain, etc.) Storing the alert and information associated with the alert can help improve the system, provide training to flight crews, and to share data with fuel providers.

The embodiments disclosed herein can comprise external (e.g., to aircraft 102 and/or fuel source 106) notification and/or performance assessment systems. In some embodiments, for example, alerting system 240 can be configured to deliver an alert and/or corresponding data (e.g., aircraft location, fuel type, contamination level, etc.) to a dashboard maintained by a fleet operator. In some embodiments, alerting system 240 can be configured to deliver an alert and/or corresponding data via e-mail, text message, push notification, etc. to a mobile computing device (e.g., a mobile phone, tablet, laptop, etc.) and/or desktop computer to notify a fleet operator, pilot, aircraft owner, etc. In some embodiments, a performance assessment system can be configured to score and/or rank fuel quality based on airports and/or Fixed Base Operators (FBO) to aid pilots and/or fleet operators in determining, for example, whether they should fly to or avoid an airport and/or whether they should obtain fuel from a particular FBO or avoid a particular FBO. In some embodiments, the fuel quality scoring and/or rankings supplied by the performance assessment system can be output to a mobile computing device configured to execute a software application. For example, the fuel quality scoring and/or rankings can be displayed on a mobile application configured to output fuel types, price, operating hours, etc. for airports and/or FBOs.

Although the embodiments disclosed herein are described in the context of alerting a flight crew of contaminated fuel as fuel enters aircraft fuel tank 104, the systems and methods can be applied during taxi and flight to similarly alert the flight crew. For example, as discussed above, fuel quality sensor 110 can be disposed in engine 120 fuel lines, cross flow valves, manifolds, transfer pumps, Auxillary Power Unit feed lines, primary feed lines, and/or any location that facilitates fuel quality sensor 110 outputting a signal corresponding to the quality of fuel entering fuel tank 104 and/or moving through aircraft's 102 fuel system. In response to an alert issued during taxi or flight, a flight crew can abort takeoff or land as soon as is safely possible. Further, although the embodiments disclosed herein reference alerting a flight crew, the embodiments can also include alerting a fueling crew, maintenance crew, or any personnel monitoring aircraft fueling.

The embodiments disclosed herein can further comprise self-test systems configured to monitor the operational status of the fuel quality systems disclosed. In some embodiments, for example, the systems disclosed herein can include a hardware performance monitoring system, auto calibration, and sensor (e.g., fuel quality sensor 110) cross-checks. For example, as discussed above, aircraft 102 can include multiple fuel quality sensors 110. Processor 112 can determine a first contamination level based on a first signal output by a first fuel quality sensor 110. Processor 112 can determine a second contamination level based on a second signal output by a second fuel quality sensor 110. If, for example, the difference between the first contamination level and the second contamination level exceeds a predetermined tolerance (e.g., 1 PPM, 2 PPM, 3 PPM, 4 PPM, 5 PPM, etc.), processor 112 can determine that the fuel quality system is not operating properly. Alerting system 240 can, for example, deliver an alert (e.g., to pilot interface 114) indicating that the fuel quality system is not operating properly and/or can suppress alerts indicating contaminated fuel.

Aspects of the fuel quality monitoring and alerting systems disclosed herein can be integrated in various fuel systems external to aircraft 102. For example, the fuel quality monitoring and alerting systems disclosed herein can be configured to determine if fuel inside fuel source 106 is contaminated before fueling aircraft 102 begins. As another example, the fuel quality monitoring and alerting systems disclosed herein can be configured to determine if fuel entering fuel source 106 (e.g., entering a fuel storage tank configured for a fuel truck) is contaminated. In some embodiments, for example, fuel quality sensor 110 can be disposed in a fuel pipeline configured to dispense fuel into fuel source 106.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. An aircraft-based fuel quality monitoring system, comprising:

a first sensor configured to output a first signal corresponding to contamination of fuel entering an aircraft fuel tank through a first fuel inlet;

a second sensor configured to output a second signal corresponding to an amount of fuel in the aircraft fuel tank;

a processor configured to determine a relative contamination level of the fuel in the aircraft fuel tank based on the first signal and the second signal; and an alerting system configured to deliver an alert via a pilot interface inside the aircraft if the relative contamination level is outside a first range.

2. The aircraft-based fuel quality monitoring system of claim 1, wherein the relative contamination level corresponds to an amount of fuel that deviates from a fuel profile.

3. The aircraft-based fuel quality monitoring system of claim 2, wherein the fuel profile comprises a ratio between a first fuel component and a second fuel component, and wherein the ratio corresponds to a fuel type.

4. The aircraft-based fuel quality monitoring system of claim 1, wherein the processor is configured to classify the fuel entering the aircraft fuel tank as one of a plurality of fuel types.

5. The aircraft-based fuel quality monitoring system of claim 4, wherein the first range corresponds to the fuel type entering the aircraft fuel tank.

6. The aircraft-based fuel quality monitoring system of claim 1, wherein the first range is between 0 PPM of water and 15 PPM of water.

7. The aircraft-based fuel quality monitoring system of claim 1, wherein the processor is configured to determine an incoming fuel contamination level based on the first signal, and wherein the alerting system is configured to deliver a second alert if the incoming fuel contamination level is outside a second range.

8. The aircraft-based fuel quality monitoring system of claim 1, wherein the processor is configured to determine an incoming fuel contamination level based on the first signal, and wherein the alerting system is configured to deliver a second alert if the incoming fuel contamination level is outside a second range and the relative contamination level is inside the first range.

9. The aircraft-based fuel quality monitoring system of claim 1, wherein the processor is configured to determine a predicted contamination level of the fuel in the aircraft fuel tank based on at least one of a fuel flow rate, a period, an expected amount of fuel, the amount of fuel in the aircraft fuel tank, or a capacity of the aircraft fuel tank.

10. The aircraft-based fuel quality monitoring system of claim 9, wherein the expected amount of fuel is based on the amount of fuel in the aircraft fuel tank and a flight plan.

11. The aircraft-based fuel quality monitoring system of claim 9, wherein the alerting system is configured to deliver a second alert if the predicted contamination level of the fuel in the aircraft fuel tank is outside the first range.

12. The aircraft-based fuel quality monitoring system of claim 1, further comprising a controller configured to actuate a valve to prevent fuel from entering the aircraft fuel tank if the relative contamination level of the fuel in the aircraft fuel tank is outside the first range.

13. The aircraft-based fuel quality monitoring system of claim 12, wherein the alerting system is configured to deliver a second alert if the controller actuates the valve.

14. The aircraft-based fuel quality monitoring system of claim 12, wherein the valve is disposed in the aircraft.

15. An aircraft comprising:
- a fuel tank;
- a first sensor configured to output a first signal corresponding to components of fuel entering the fuel tank;
- a second sensor configured to output a second signal corresponding to an amount of fuel in the fuel tank;
- a processor configured to determine the components of fuel entering the fuel tank; and
- an alerting system comprising a pilot interface and configured to deliver an alert based on the components of fuel entering the fuel tank and the amount of fuel in the fuel tank.

16. The aircraft of claim 15, wherein the processor is configured to determine a predicted proportion of a first fuel type inside the fuel tank based on at least one of a fuel flow rate, a period, an expected amount of fuel, the amount of fuel in the fuel tank, or a capacity of the fuel tank.

17. The aircraft of claim 16, wherein the alerting system is configured to deliver the alert if the predicted proportion of the first fuel type inside the fuel tank is below a minimum proportion.

18. The aircraft of claim 17, wherein the minimum proportion is between 0.95 and 0.99.

19. The aircraft of claim 16, wherein the first fuel type corresponds to a fuel type that is compatible with the aircraft.

20. The aircraft of claim 16, further comprising a controller configured to actuate a valve to prevent fuel from entering the fuel tank if the predicted proportion of the first fuel is below a minimum proportion.

21. The aircraft of claim 16, wherein a controller is configured to actuate a valve to prevent fuel from entering the fuel tank if the predicted proportion is below a minimum proportion and the controller receives input from a pilot input system.

22. The aircraft of claim 16, wherein a controller is configured to actuate a valve to prevent fuel from entering the fuel tank if the predicted proportion is below a minimum proportion for a consecutive number of epochs.

23. The aircraft of claim 15, wherein the processor is configured to classify the fuel entering the fuel tank as one of a plurality of fuel types.

24. The aircraft of claim 23, wherein the alerting system delivers the alert to a display configured to output text corresponding to the fuel type entering the aircraft.

25. The aircraft of claim 23, wherein the alerting system is configured to deliver a second alert if the fuel type entering the aircraft is different from a first fuel type.

26. The aircraft of claim 25, wherein the alerting system is configured to deliver the second alert with an alert level corresponding to the fuel type entering the aircraft.

27. An aircraft-based fuel quality monitoring system, comprising:
- a first sensor configured to output a first signal corresponding to contamination of fuel entering an aircraft fuel tank of an aircraft through a first fuel inlet;
- a second sensor configured to output a second signal corresponding to an amount of fuel in the aircraft fuel tank;
- a processor configured to determine a relative contamination level of the fuel in the aircraft fuel tank based on the first signal and the second signal; and
- an alerting system configured to deliver a message via a pilot interface inside the aircraft corresponding to the relative contamination level.

28. The aircraft-based fuel quality monitoring system of claim 27, wherein the message comprises a numeric value corresponding to the relative contamination level.

29. The aircraft-based fuel quality monitoring system of claim 27, wherein the message comprises a percentage corresponding to the relative contamination level.

30. The aircraft-based fuel quality monitoring system of claim 27, wherein the message comprises a fuel quality classification.

* * * * *